US007285651B2

(12) United States Patent
Lander et al.

(10) Patent No.: US 7,285,651 B2
(45) Date of Patent: *Oct. 23, 2007

(54) PROCESS FOR THE SCALEABLE PURIFICATION OF PLASMID DNA

(75) Inventors: Russel Jackson Lander, Lansdale, PA (US); Michael Albert Winters, Doylestown, PA (US); Francis Jeremiah Meacle, London (GB)

(73) Assignee: Merck & Co., Inc., Rahway, NJ (US)

( * ) Notice: Subject to any disclaimer, the term of this patent is extended or adjusted under 35 U.S.C. 154(b) by 423 days.

This patent is subject to a terminal disclaimer.

(21) Appl. No.: 10/922,324

(22) Filed: Aug. 19, 2004

(65) Prior Publication Data

US 2005/0019896 A1    Jan. 27, 2005

Related U.S. Application Data

(63) Continuation of application No. 10/113,374, filed on Apr. 1, 2002, now Pat. No. 6,797,476, which is a continuation of application No. 09/875,379, filed on Jun. 6, 2001, now abandoned, which is a continuation-in-part of application No. 09/745,217, filed on Dec. 21, 2000, now abandoned.

(60) Provisional application No. 60/171,472, filed on Dec. 22, 1999.

(51) Int. Cl.
*C12P 21/02* (2006.01)

(52) U.S. Cl. .................................. 536/23.1; 435/320.1

(58) Field of Classification Search ..................... None
See application file for complete search history.

(56) References Cited

U.S. PATENT DOCUMENTS

| | | | |
|---|---|---|---|
| 4,923,978 A | 5/1990 | McCormick | |
| 5,075,430 A | 12/1991 | Little | |
| 5,523,392 A | 6/1996 | Woodard et al. | |
| 5,525,319 A | 6/1996 | Woodard et al. | |
| 5,576,196 A | 11/1996 | Horn et al. | |
| 5,707,812 A | 1/1998 | Horn et al. | |
| 5,808,041 A | 9/1998 | Padhye et al. | |
| 6,193,891 B1 | 2/2001 | Kent et al. | |
| 6,797,476 B2 * | 9/2004 | Lander et al. | 435/6 |

FOREIGN PATENT DOCUMENTS

| | | |
|---|---|---|
| WO | WO96/02658 A1 | 2/1996 |
| WO | WO96/36706 | 11/1996 |
| WO | WO97/10331 | 3/1997 |
| WO | WO98/01464 | 1/1998 |
| WO | WO98/04730 | 2/1998 |

OTHER PUBLICATIONS

Jones, A.S.: "Use of Alkyltrimethylammonium bromides for the Isolation of Ribo-and Deoxyribo-nucleic Acids" Nature, vol. 199, No. 4890, Jul. 20, 1963, pp. 280-282.
Winters, Michael A. et al: "Plasmid DNA purification by selective calcium silicate adsorption of closely related impurities." Biotechnology Progress, vol. 19, No. 2, Jan. 31, 2003, pp. 440-447.
Del Sal, G. et al., "The CTAB-DNA Precipitation Method: A Common Mini-Scale Preparation of Template DNA from Phagemids, Phages or Plasmids Suitable for Sequencing", 1989, BioTechniques, vol. 7, pp. 514-519.
Vogelstein, B. & Gillespie, D., "Preparative and analytical purification of DNA from agarose", 1979, Proc. Natl. Acad. Sci. USA, vol. 76, pp. 615-619.
Boom, R. et al., "Rapid and Simple Method for Purification of Nucleic Acids", 1990, Journal of Clinical Microbiology, vol. 28, pp. 495-503.
Carter, M. & Milton, I., "An inexpensive and simple method for DNA purifications on silica particles", 1993, Nucleic Acids Research, vol. 21, p. 1044.
Birnboim, H. & Doly, J., "A rapid alkaline extraction procedure for screening recombinant plasmid DNA", 1979, Nucleic Acids Research, vol. 7, pp. 1513-1523.
Gustincich, S. et al., "A Fast Method for High-Quality Genomic DNA Extraction from Whole Human Blood", 1991, BioTechniques, vol. 11, pp. 298-301.
Ishaq, M. et al., "Large-Scale Isolation of Plasmid DNA Using Cetyltrimethylammonium Bromide", 1990, BioTechniques, vol. 9, pp. 19-24.
Prazeres, D. et al., "Large-scale production of pharmaceutical-grade plasmid DNA for gene therapy: problems and bottlenecks", 1999, TIB Tech, vol. 17, pp. 169-174.
Basha, S. & Palanivelu P., "Two simple non-enzymatic procedures to isolate high molecular weight DNA from fungi", 1995, Current Science, vol. 68, pp. 587-588.
Sambrook J. et al. "Molecular Cloning" 1989, Cold Spring Harbor Laboratory Press, pp. E-10-E.14.

* cited by examiner

*Primary Examiner*—James Ketter
(74) *Attorney, Agent, or Firm*—Laura M. Ginkel; Sheldon O. Heber

(57) ABSTRACT

The present invention relates to a nonchromatographic-based process for the isolation of clinical grade plasmid DNA from bacterial cells. The exemplified methods described herein outline a scaleable, economically favorable protocol for the purification of clinical grade plasmid DNA from *E. coli* which includes CTAB-based precipitation of DNA in combination with adsorption of impurities to calcium silicate.

13 Claims, 8 Drawing Sheets

PROCESS FOR THE SCALEABLE PURIFICATION OF PLASMID DNA

CROSS-REFERENCE TO RELATED APPLICATIONS

This application is a continuation of U.S. application Ser. No. 10/113,374, filed Apr. 1, 2002, now U.S. Pat. No. 6,797,476, which is a continuation of U.S. application Ser. No. 09/875,379, filed Jun. 6, 2001, now abandoned, which is a continuation-in-part of U.S. application Ser. No. 09/745,217, filed Dec. 21, 2000, now abandoned which claims the benefit, under 35 U.S.C. 119(e), of U.S. provisional application No. 60/171,472, filed Dec. 22, 1999.

STATEMENT REGARDING FEDERALLY-SPONSORED R&D

Not Applicable

REFERENCE TO MICROFICHE APPENDIX

Not Applicable

FIELD OF THE INVENTION

The present invention relates to scaleable methods of isolating clinical grade plasmid DNA from microbial cells. The exemplified methods described herein outline a scaleable, economically favorable protocol for the purification of clinical grade plasmid DNA from *E. coli* which does not rely on expensive chromatography steps during downstream processing of the plasmid preparation, thus making this methodology especially amenable to large scale commercial plasmid purification procedures.

BACKGROUND OF THE INVENTION

Advances in the areas of gene therapy and DNA vaccination have created a need for the large scale manufacture and purification of clinical-grade plasmid DNA. As pointed out in a recent review (Prazeres, et al., 1999, *TIBTech* 17: 169-174), despite previous work on small scale plasmid DNA purification methodology, it has been difficult to scale up the manufacture and purification of clinical-grade plasmid DNA. Especially problematic have been downstream processing steps, which for the most part have relied on alkaline lysis of the harvested cells, followed by ammonium acetate precipitation and further downstream processing steps relying heavily on size exclusion, anion exchange and reversed phase chromatography steps. In addition, it should be noted that the expense of raw materials, such as resins and buffers, for multiple chromatographic steps become prohibitive due high unit cost and poor capacity for the large DNA molecules. It is known that the cationic detergent CTAB and various forms of silica have been used for the small scale plasmid DNA preparations and not designed to produce clinical grade plasmid vaccine. The ability of these steps to remove certain impurities has not been recognized nor has their utility for scalable process design. Del Sal et al. (1989, *BioTechniques* 7(5): 514-519) and Gustincich et al. (1991, *BioTechniques* 11(3): 298-301) use CTAB to precipitate plasmid DNA from clarified small scale *E. coli* lysates and genomic DNA from small scale preparations of whole human blood, respectively. Ishaq et al. (1990, *Biotechniques* 9(1): 19-24) disclose the application of small scale CTAB-precipitated plasmid DNA to a PZ523 spin column, yielding a purified product which is at least suitable as a template for subcloning and dideoxy sequencing. None of this art teaches or suggests the use of detergent-based precipitation steps to produce clinical grade lots of DNA plasmid.

Vogelstein & Gillespie (1979, *Proc. Natl. Acad. Sci. USA.* 76(2): 615-619) disclose a technique for separating restriction enzyme digests of DNA from agarose gels, in which DNA in the presence of concentrated sodium iodide is bound to glass (silica), washed with ethanol, and eluted at a low salt concentration. Boom et al. (1990, *J. Clin. Microbiol.* 28(3): 495-503) and Carter & Milton (1993, *Nucleic Acids Res.* 21(4): 1044) disclose methods for the isolation of plasmid DNA which is suitable for DNA sequencing. Plasmid DNA in the presence of the chaotropic agent guanidinium thiocyanate is bound to silica in the form of diatomaceous earth. The immobilized plasmid DNA is washed with ethanol and eluted at low salt concentrations. Subtle variations of this technique are disclosed in (1) PCT Publication WO 91/10331; (2) PCT Publication WO 98/04730, as well as (3) U.S. Pat. No. 5,075,430, issued to Little on Dec. 24, 1999, which discloses a method of isolating plasmid DNA which depends upon adsorption of the DNA onto diatomaceous earth in the presence of a chaotropic agent followed by separation and elution of the DNA; and (4) U.S. Pat. No. 5,808,041, issued to Padhye et al. on Sep. 15, 1998, which discloses a method of nucleic acid isolation utilizing a composition comprising silica gel and glass particles in the presence of a chaotropic agent. Again, these techniques have not been successfully applied to methodology for large scale DNA plasmid preparations required for generation of gram quantities of plasmid DNA for clinical grade formulations for administration to humans and other potential hosts.

U.S. Pat. No. 4,923,978, issued to McCormick on May 8, 1990, discloses the use of silica to purify DNA by preferentially binding proteinaceous materials.

U.S. Pat. No. 5,576,196, issued to Hom et al. on Nov. 19, 1996, discloses the use of silica to purify DNA by preferentially binding RNA.

U.S. Pat. Nos. 5,523,392 and 5,525,319, issued to Woodard et al. on Jun. 4, 1996 and Jun. 11, 1996, respectively, disclose boron silicates, phosphosilicates, and aluminum silicates which can be used as binding surfaces for DNA purification.

PCT International Application PCT/US96/20034 (International publication No. WO 98/01464) discloses the use of hydrated calcium silicate to selectively separate organic compounds from biological fluids, such as blood.

Again, none of the above-identified references provide adequate guidance to the artisan of ordinary skill to provide a methodology to prepare scalable, clinical grade DNA plasmid lots which are substantially free of host cell protein, host cell endotoxin, genomic DNA, genomic RNA and plasmid degradates such as linear and open circle forms. To this end, it would be extremely useful to identify a scaleable plasmid purification process which eliminates the requirement of prohibitively expensive chromatography steps while also providing for gram quantities of a DNA plasmid preparation which is clinical grade for use in at least human vaccination and human gene therapy applications. The present invention addresses and meets these needs by disclosing a scaleable plasmid purification process which preferably utilizes a cationic detergent such as CTAB to selectively precipitate plasmid DNA in an upstream step in combination with downstream large scale batch adsorption steps using hydrated, crystalline calcium silicate (herein, "hcCaSiO$_3$") or any similar acting compound to remove remaining contaminants such as genomic DNA, genomic RNA, protein, host endotoxin and plasmid degradates such as linear and open circle forms.

SUMMARY OF THE INVENTION

The present invention relates to methods of isolating clinical-grade plasmid DNA from microbial cells, methods representing a scaleable, economical manufacturing process which provides alternatives for production and purification of large scale, clinical-grade plasmid DNA. The present invention relates further to several post-lysis core processes which contribute to the scaleable, economical nature of the DNA plasmid purification process. More specifically, post-lysis steps include, but are not limited to, (1) a two part precipitation/dissolution step were plasmid DNA is precipitated with a detergent (such as CTAB) either in a single or stepwise fashion, coupled with concentration and selective dissolution of the CTAB-precipitate plasmid DNA with a salt solution; (2) removal of endotoxin and other remaining impurities by adsorption onto hydrated, crystallized calcium silicate ($hcCaSiO_3$), again, either in a single or stepwise fashion; and; (3) concentration of the purified plasmid DNA by alcoholic precipitation (including but not limited to ethanol, methanol and isopropanol), or another concentrating method, including but not limited to ultrafiltration. These steps may be used in combination, in further combination with additional purification steps known in the art, and/or wherein at least one of the above-mentioned steps is omitted, preferably in combination with other methodology known in the art to be associated with DNA plasmid purification technology.

The methods of the present invention allow for clinical grade DNA plasmid purification from microbial cells including but not limited to bacterial cells, plant cells, yeast, baculovirus, with E. coli being the preferred micorbial host. The clinical grade plasmid DNA purified by the methods described herein is extremely useful for administration to humans as a vaccine or gene therapy vehicle.

An advantage of the plasmid purification process of the present invention is in part due to the finding that stepwise precipitation of DNA with CTAB in conjunction with removal of remaining impurities by adsorption onto $hcCaSiO_3$ removes problematic impurities, including genomic DNA, RNA and DNA degradates such as linear DNA, with a heretofore unrecognized selectivity. A complete process design incorporating these precipitation/purification steps is at the core of the invention disclosed herein. The disclosed process is also scalable.

Another advantage of the purification process of the present invention is the elimination of the need for costly polymer-based chromatography resins through the alternative approach of selective precipitation and adsorption for large scale plasmid preparations.

Another advantage of the purification process of the present invention is that it is fundamentally amenable to manufacturing scale operation. The unit operations consist of precipitation, filtration, adsorption and drying. The use of diatomaceous earth affords an incompressible filter cake while avoiding fouling problems often associated with fermentation products.

Another advantage of the purification process of the present invention is that it avoids the need for adding recombinant RNase, an expensive enzyme, for the removal of RNA at more or more steps during the process.

Another advantage of the purification process of the present invention is that precipitation with a long chain detergent such as CTAB affords reductions in downstream processing volumes which are important in the disposal of solvent containing waste streams at the manufacturing scale.

Yet another advantage of the purification process of the present invention is that alcohol (such as ethanolic) precipitation is an ideal way to gain a stable bulk product which can be resuspended at high concentrations without the anticipated shear damage which occurs during membrane based concentration.

It is an object of the present invention to provide a cost effective process for the large scale purification of clinical grade plasmid DNA from prokaryotic hosts such as E. coli.

It is further an object of the present invention to provide for post-lysis steps which result in scaleable, economic process for the large scale (i.e., scaleable) purification of plasmid DNA, including but not limited to the post-lysis steps of (i) precipitation of plasmid DNA with a detergent (such as CTAB) either in a single or stepwise fashion, coupled with concentration and selective dissolution of the CTAB-precipitate plasmid DNA with a salt solution; (ii) removal of endotoxin and other remaining impurities by adsorption onto hydrated, crystallized calcium silicate ($hcCaSiO_3$) in either in a single or stepwise fashion; and/or, (iii) concentration of the purified plasmid DNA by alcohol (such as ethanol precipitation) or another concentrating method, including but not limited to ultrafiltration. These steps may be used in combination, in further combination with additional purification steps known in the art, and/or wherein at least one of the above-mentioned steps is omitted, preferably in combination with other methodology known in the art to be associated with DNA plasmid purification technology.

It is a further object of the present invention to provide methods for a cost effective process for large scale (i.e., scaleable) purification of clinical grade plasmid DNA from prokaryotic hosts which comprises the steps of: (i) cell lysis; (ii) lysate clarification with diatomaceous earth-aided filtration; (iii) selective precipitation of plasmid DNA using cetyltrimethylammonium bromide (CTAB), followed by filtration to recover a plasmid DNA-containing filter cake; (iv) selective dissolution of the plasmid DNA-containing filter cake with salt solution; (v) adsorption of residual impurities onto calcium silicate hydrate followed by filtration; and (vi) precipitation of purified plasmid DNA using alcohol (including but not limited to alcohol).

As used interchangeably herein, the terms "clinical grade plasmid DNA" and "pharmaceutical grade plasmid DNA" refer to a preparation of plasmid DNA isolated from prokaryotic cells which is of a level of purity acceptable for administration to humans for any known prophylactic or therapeutic indication, including but not limited to gene therapy applications and DNA vaccination applications.

As used herein, "non-supercoiled plasmid DNA" refers to any DNA that is not supercoiled plasmid DNA, including any other form of plasmid DNA such as nicked open circle and linear as well as host genomic DNA.

As used herein, "CTAB" refers to —hexadecyltrimethylammonium bromide— or —cetyltrimethylammonium bromide—.

As used herein, "$hcCaSiO_3$" refers to —hydrated, crystalline calcium silicate—.

As used herein, "STET buffer" refers to a buffer comprising approximately 50 mM Tris-HCl (~pH 7.0-9.0), about 50-100 mM EDTA, about 8% Sucrose, and about 2% Triton®-X100.

As used herein, "IPA" refers to —isopropanol—.
As used herein, "PEG" refers to —polyethylene glycol—.
As used herein, "GDNA" refers to —genomic DNA—.
As used herein, "gRNA" refers to —genomic RNA—.

As used herein, "LRA™" refers to —lipid removal agent™—.

As used herein, "EDTA" refers to —ethylenediaminetetraacetic acid—.

As used herein, "SC" refers to —supercoiled—.

As used herein, "OC" refers to —open circular—.

As used herein, "NTU" refers to —normalized turbidity units—.

As used herein, "L" refers to—liters—.

As used herein, "HPLC" refers to—high performance liquid chromatography—.

DETAILED DESCRIPTION OF THE INVENTION

Figure 1:
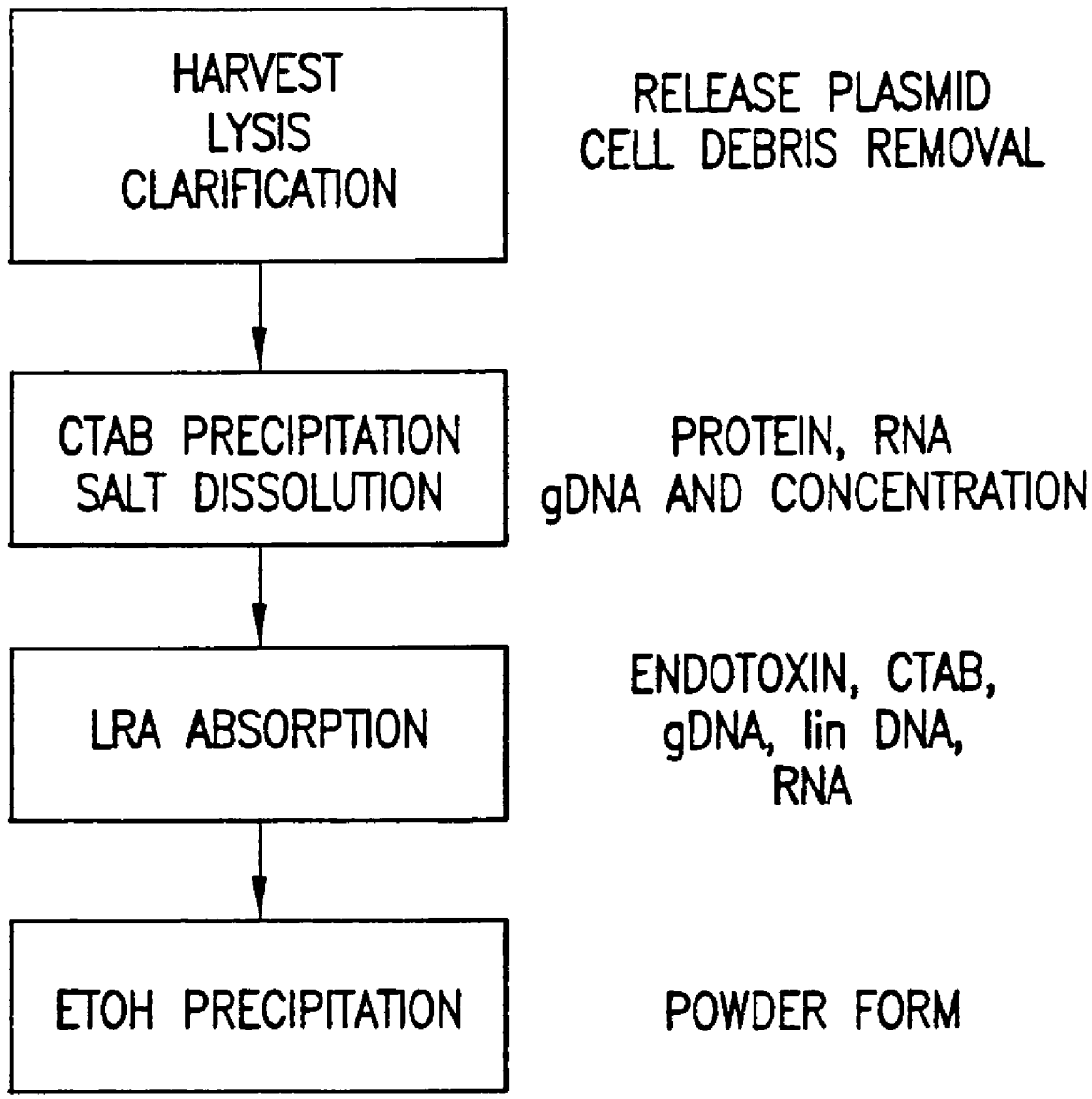
FIG. 1 shows the process flow diagram comprising a core four step process which removes cell debris by clarification. CTAB stepwise precipitation and calcium silicate adsorption remove host RNA, DNA, protein and endotoxin as well as plasmid degradates open circle and linear DNA. A stable bulk powder is created by ethanolic precipitation.

The present invention relates to a scaleable methodology representing inexpensive manufacturing alternatives for production of clinical-grade plasmid DNA. More specifically, a core of the invention relates to several downstream (i.e., post-lysis) steps which include (1) a two part precipitation/dissolution step were plasmid DNA is precipitated with a detergent (such as CTAB) either in a single or stepwise fashion, coupled with concentration and selective dissolution of the CTAB-precipitate plasmid DNA with a salt solution; (2) removal of endotoxin and other remaining impurities by adsorption onto hydrated, crystallized calcium silicate (hcCaSiO$_3$), again, either in a single or stepwise fashion; and; (3) concentration of the purified plasmid DNA by alcohol (including but not limited to ethanol-, methanol- or isopropanol-based precipitation or another concentrating method, including but not limited to ultrafiltration. As is exemplified herein, steps (1) and (2) are associated with subsequent filtration steps to physically separate various cell lysate impurities from to object of the purification process, the supercoiled plasmid DNA.

It is within the scope of the present invention to add or subtract from these three core steps to formulate an overall scaleable purification process which results in recovery of clinical grade plasmid DNA. Therefore, it is intended that either the detergent-based plasmid DNA precipitation step or the hcCaSiO$_3$ adsorption step may be omitted. This streamlined process may include additional "non-core" steps to complement the overall purification scheme. For example, a preferred process of the present invention may incorporate an initial detergent-based precipitation step with a final step of concentrating the plasmid DNA by ethanol precipitation. These two core steps might then be combined with other purification steps known in the art (such as column chromatography) to produce a clinical grade lot of plasmid DNA. However, core steps of (1) detergent precipitation and selective salt dissolution, (2) adsorption to hcCaSiO$_3$ and (3) plasmid DNA concentration, will more likely provide the basis from which to expand the purification procedures to result in an overall scaleable process incorporating additional complementary steps. These complementary steps may be added at the discretion of the artisan, depending on the overall quality of plasmid DNA which is required for a specific lot. To this end, various examples of using these three core steps as a basis for an overall scaleable process are presented herein to exemplify, but certainly not limit, the present invention. The skilled artisan may look to known plasmid purification steps to provide for a scheme which results in an appropriate grade of DNA plasmid purity. For example, PCT International Application Nos. PCT/US95/09749 (WO96/02658) and PCT/US96/07083 (WO96/36706) give guidance as to alternative, chromatography-based downstream steps which may be utilized in combination with the core purification steps mentioned in this paragraph to provide an effective purification protocal. Both disclosures show downstream events (subsequent to a heat exchange step) which includes clarification, ultrafiltration with benzonase for DNA and protein removal, ion exchange for more protein and reversed phase chromatography for endotoxin, Lin/OC impurities and a final ultrafiltration to concentrate. Accordingly, if CTAB alone is employed, it might replace ultrafiltration and ion exchange but it would be used in conjunction with a final reversed phase chromatography step to remove impurities which had not been removed by CTAB. On the other hand, if only hcCaSiO$_3$ is employed, such a protocal could be preceded by clarification, ultrafiltration and ion exchange chromatography as described in WO96/02658 and WO96/36706.

One embodiment of the present invention relates to a method of purifying supercoiled plasmid DNA from a cell lysate of a microbial fermentation which comprises precipitating supercoiled plasmid DNA by a detergent-induced precipitation. This portion of the invention is exemplified, but not limited to, use of the detergent cetyltrimethylammonium bromide (CTAB). The detergent of interest may be added in a single or stepwise fashion. An example of stepwise addition of the detergent is the stepwise addition of CTAB (in this case, feeding a 1% w/v CTAB solution to clarified lysate in STET buffer) with a first CTAB-induced precipitation from about 0.25% to about 0.28% to precipitate out debris and non-supercoiled plasmid DNA, followed by a second CTAB-induced precipitation from about 0.30% to about 0.33% to precipitate the supercoiled plasmid DNA, these ranges best coinciding with the use of a standard STET lysis buffer (approximately 50 mM Tris-HCl (~pH 7.0-9.0), about 50-100 mM EDTA, about 8% Sucrose, and about 2% Triton®-X100). It will be within the purview of the skilled artisan to alter stepwise precipitation ranges to adjust to any peculiarities of various buffer systems, including but not necessarily limited to the inclusion of a Triton®-based detergent or the divalent cation EDTA within the lysis buffer, such that a workable amount of impurities are first precipitated away from the remaining buffer solution comprising supercoiled plasmid DNA, which is then precipitated with an additional CTAB-induced precipitation. As noted above in reference to use of a standard STET buffer, it will also be useful to add compounds such as EDTA and/or Triton®-based detergents in useful concentrations to the various buffers to help promote precipitation of plasmid DNA. To this end, a STET buffer is useful as a cell lysis buffer by containing effective amounts of Triton® and EDTA. These compounds are thus present during the lysis step, with EDTA inhibiting DNAase activity by associating with divalent metal ions which otherwise activate DNAase. In addition, Triton® dissolves the *E. coli* cell membrane. Both components are carried to the CTAB step(s). EDTA continues to play a favorable role since the divalent metal ions will prevent complexation of plasmid with CTAB. More importantly is the effect of Triton® in selecting an effective CTAB concentration for either a single or stepwise cut to precipitate supercoiled plasmid DNA. Triton® interacts with CTAB, making it necessary to add CTAB to a certain threshold level (e.g., 0.23%, 0.25%, 0.30%, etc., based on a 1% CTAB feed solution added to a clarified lysate in STET buffer) before supercoiled plasmid DNA can precipitate. Therefore, the CTAB concentration range is dependent upon both the Triton® and DNA concentration. To this end, a stepwise range of, for example, 0.25-0.28% CTAB and 0.28-0.33% CTAB (again, based on a feed of 1% w/v of CTAB) is predicated on the following: the low cut quantity is a function of the Triton® concentration, since Triton® binds 22 molecules of CTAB per Triton® micelle, each micelle assumed to contain 140 Triton molecules, while the high cut quantity is a function of the concentration of DNA concentration since each plasmid molecule binds 0.9 equivalents of CTAB per DNA nucleotide repeat unit. In this particular case which is outlined in Example 1, the cited range of 0.25-0.28% CTAB for low cut precipitation corresponds to the addition of a 1% CTAB solution to a lysate STET buffer which contains 1% Triton. The high cut range of 0.28-0.33% corresponds to the addition of a 1% CTAB solution to the filtered low cut solution which was derived from an original clarified lysate solution which contained 0.34 mg/ml plasmid DNA of about 84% purity. The artisan may best match the amount of CTAB (for either a single or stepwise precipitation of supercoiled plasmid DNA) with a particular buffer either as described in Example Section 1 (visual inspection of DNA precipitation) or Example Section 2 (using a particle-size analyzer to inspect DNA precipitation). In the latter example when using a standard STET buffer, the artisan will watch for precipitation by a Lasentec® turbidity real time probe, knowing that it is finished at around 0.25% by correlating this CTAB concentration to the Triton® concentration, which is constant from batch to batch (established at lysis). The same procedure is then completed with Lasentec® as DNA precipitates, knowing there is about 1 mg/ml of DNA which corresponds to the increment of 0.03% (0.25 to 0.28 differential) required to precipitate. The artisan will be aware of these numbers in case no Triton® (or Triton® concentrations which differ from a standard STET buffer), as with a NaOH/KOAc lysis approach, or if the fermentation results in a very different concentration of plasmid. Therefore, the former affects the low cut and the latter affects the high cut amount of CTAB. It is preferred that a low and high cut range be determined by a particle size analyzer, such as a Lasentec® particle size analyzer. This method increases accuracy to more closely define low and high cut ranges, as the CTAB precipitation of plasmid occurs over a tight CTAB range. Therefore, these ranges may be approximated by measuring important variables (such as Triton® and plasmid DNA concentration) and may also be specifically identified by either the visual, or preferably machine guided analysis of particles in solution at various CTAB concentrations. It is exemplified herein that use of a standard STET buffer and a 1% w/v CTAB solution (in 40 mM NaCl) results in optimal low and high CTAB cuts of approximately 0.25-0.28% w/v (low) and 0.30-0.33% (high). It will be understood that such values apply to situations in which CTAB is fed to the clarified lysate in STET buffer using a 1% w/v CTAB feed solution. It is acceptable, for example only, to double the concentration of the CTAB feed solution (e.g., a 2% w/v CTAB feed) and add half the volume (for the same mass of CTAB). In this case, the low cut and high cut concentrations would be roughly 0.29-0.33% and 0.35-0.40%, respectively. These figures are easily normalized by converting from a numerical value based on a weight/volume percentage (% w/v) to a simple process based on CTAB mass added per liter of clarified lysate. For example, in the same scenario as exemplified in Example Section 1 (a standard STET buffer) a low cut CTAB concentration would be reached by adding from 3.3 to 3.9 g of CTAB per liter of clarified lysate, while a high cut CTAB concentration would be reached by adding (beyond the initial low cut addition) CTAB to a final amount of from 4.3 to 5.0 g of CTAB per liter of clarified lysate. A single or stepwise CTAB-based detergent step will be associated with a filtration step to generate a filter cake precipitate (containing supercoiled plasmid DNA) for subsequent salt dissolution. In addition, a preferred downstream step remains the concentration of supercoiled plasmid DNA by ethanol precipitation or ultrafiltration. The use of an alcohol-based (such as ethanol) precipitation is preferred in that it is possible, as shown herein, to finally precipitate and further concentrate supercoiled DNA by ethanol precipitation, resulting in a powder precipitate containing the supercoiled plasmid DNA. It will be evident that this downstream step may by utilized with any of the various combinations of earlier steps to finally purify supercoiled plasmid DNA away from any remaining impurities while also concentrating the plasmid DNA and allowing for resuspension into a more workable buffer volume. This embodiment also entails process(es) described in this paragraph in combination with at least the addition of a step which includes but is not necessarily limited to clarification of the cell lysate prior to addition of CTAB. Diatomaceous earth (DE) is used to exemplify this step, but other components may be substituted for DE to clarify the cell lysate, including but not limited to other cellulose-based filter aids such as Solka Floc and Esosorb (Graver). The DE or other material used to clarify the cell lysate may be removed by any liquid solid separation technique known in the art, including but by no means limited to filtration and centrifugation. Any process incorporating a lysate clarification step may also incorporate the concentration steps disclosed herein, including but not limited to ethanol precipitation or ultrafiltration, as discussed herein.

Figure 4A:
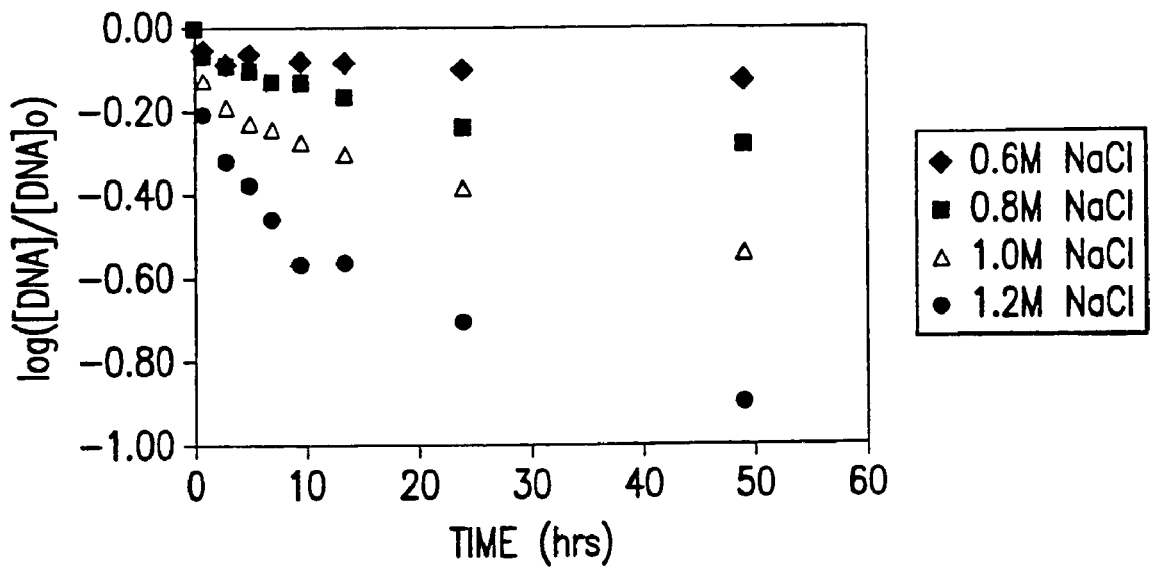
FIGS. 4A-D shows purification by adsorption of impurities to hcCaSiO$_3$ (LRA™). (A). Equilibrium adsorption of plasmid DNA vs. sodium chloride concentration. (B). Adsorption of genomic or host DNA as measured by qPCR. LRA™ selectively removes DNA after 5 hr of mixed contacting at 1.2 M NaCl concentration. Plasmid yield is ca. 60%. (C) Selective adsorption of plasmid degradates onto hcCaSiO$_3$ in 1.2 M NaCl. Agarose gel electrophoresis of liquid-phase samples in contact with hcCaSiO$_3$ as a function of hcCaSiO$_3$ concentration (lane 1: 32 g hcCaSiO$_3$/g DNA; lane 2: 35 g hcCaSiO$_3$/g DNA; lane 3: 40 g hcCaSiO$_3$/g DNA; lane 4: 42 g hcCaSiO$_3$/g DNA; lane 5: 45 g hcCaSiO$_3$/g DNA). Linear, relaxed open circle and multimers (M) are removed. (D) Selective adsorption of plasmid degradates onto hcCaSiO$_3$ in 0.5 M NaCl. Agarose gel electrophoresis of liquid-phase samples in contact with 32 g of hcCaSiO$_3$ per g of total DNA as a function of time (lane 1: 3.3 hr, lane 2: 6.2 hr, lane 3: 10.8 hr, lane 4: 21.5 hr). Linear, relaxed open circle, and multimers (M) are removed.

Another embodiment of the present invention relates to a method of purifying supercoiled plasmid DNA from a cell lysate of a microbial fermentation wherein a core step is the addition of hydrated, crystallized calcium silicate (hcCaSiO$_3$) to the cell lysate. It is shown herein that either a single or stepwise addition of hcCaSiO$_3$ to the cell lysate results in adsorption of residual impurities away from the supercoiled plasmid DNA. As noted above, another aspect of this portion of the invention relates to the adsorption step(s) in the previous paragraph in conjunction with at least the addition of a step which includes but is not necessarily limited to clarification of the cell lysate prior to addition of CTAB. Again, DE exemplifies, but does limit this additional step. Any of the combination of process steps referred to in this paragraph may also incorporate a step of concentrating the supercoiled plasmid DNA, including but not limited to ethanol precipitation or ultrafiltration, as described herein. The addition of one or more steps beyond a hcCaSiO$_3$ adsorption step (such as lysate clarification and/or a concentration step with ethanol or ultrafiltration) may occur whether single or stepwise adsorption steps are utilized. At this stage of a core purification scheme the primary impurities are CTAB, endotoxin, genomic DNA and plasmid degradates. Other residual impurities (present at lower concentrations) include proteins, RNA, and perhaps Triton®. Hydrated calcium silicate will bind all of these impurities. The precise amount of hcCaSiO$_3$ required for addition is governed by (1) the amount of impurity present; (2) the buffer conditions (i.e., salt concentration) and (3) perhaps other variables which include the temperature and the type of salt utilized throughout the purification process. The amount of impurities present may depend upon but are not necessarily limited to (i) how much CTAB was added, if any was used at all, (ii) lot-to-lot differences in fermentation broth which could affect the mass of genomic DNA, plasmid degradates, and endotoxin, and (iii) the lysis procedure employed, which could also affect the amount of genomic DNA, plasmid degradates, and endotoxin. In view of these variables, it will be evident that the amount of hcCaSiO$_3$ to be added during a specific run may vary. It is anticipated that an amount of hcCaSiO$_3$ to be added would be in the range of up to about 200 grams/liter, depending upon the conditions described above as well as potential differences depending on the lot of hcCaSiO$_3$ made available during that specific run. Example section 1 gives guidance in a range from about 25 grams/liter to about 75 grams/liter. But again, the conditions for hcCaSiO$_3$ adsorption may scale upward or downward in relation to the conditions explained above, thus potentially necessitating addition of hcCaSiO$_3$ at a higher end of the range, toward 200 grams/liter. In addition, it is shown herein that a higher concentration of NaCl increases the capacity of LRA™ for DNA and other impurities. The effect of LRA™ for plasmid DNA only is shown in FIG. 4A, but high salt concentration also seem to increase the capacity LRA™ for binding genomic DNA and other impurities. Therefore, it will be useful in some instances to consider higher salt concentrations, which should allow for the use of a less amount of the respective hcCaSiO$_3$. It is expected that useful salt concentrations may be in a range from, for example with NaCl, up to about 5M NaCl.

Another embodiment of the present invention relates to a purifying supercoiled plasmid DNA from a cell lysate of a microbial fermentation, which comprises incorporation of three distinct process steps, namely (i) precipitating the supercoiled plasmid DNA by a detergent-induced precipitation and redissolving the resultant filter cake in a salt solution; (ii) adding hcCaSiO$_3$ to the redissolved supercoiled plasmid to adsorb residual impurities away from the supercoiled plasmid DNA, resulting in a solution containing the supercoiled plasmid DNA; and, (iii) concentrating the supercoiled plasmid DNA. Again, an exemplified detergent is CTAB, which can be added in a single or stepwise fashion, exemplified herein in part by a stepwise addition of the detergent (CTAB, as a 1% w/v feed) in a STET-based lysate buffer with a first cut at a [CTAB] from about 0.25% to about 0.28% and a second cut at a [CTAB] from about 0.30% to about 0.33%. As noted throughout this specification (and exemplified in Example section 1 (visual indication) and Example section 2), it is within the purview of the skilled artisan, with this specification in hand, to alter stepwise precipitation ranges to adjust to any peculiarities of various buffer systems, such that a workable amount of impurities are first precipitated away from the remaining buffer solution comprising supercoiled plasmid DNA, which is then precipitated with an additional CTAB-induced precipitation. Again, it will also be useful to add buffer components such as EDTA and/or Triton-based detergents in useful concentrations to the various buffers to help promote precipitation of plasmid DNA. A salt dissolution of the recovered filter cake (comprising supercoiled plasmid DNA) is performed in a buffer solution of optimal ionic strength and composition. Salt is added to an optimal concentration to dissolve plasmid while not dissolving genomic DNA and other impurities. This concentration is determined by measuring the concentration of supercoiled plasmid in solution at various salt increments or, indirectly by measuring the solution viscosity. Additional steps (one or any combination) to the above-mentioned core steps may include but are not limited to lysate clarification and/or a concentration step with ethanol or ultrafiltration, as discussed herein.

Another embodiment encompasses the incorporation of additional steps, namely an initial clarification of the cell lysate, to the core process to provide for an improved purification scheme. This particular embodiment of the invention comprises downstream processing steps which include (i) lysate clarification, preferably with diatomaceous earth-aided filtration or centrifugation (ii) single or stepwise precipitation of plasmid DNA with a detergent, such as CTAB, salt dissolution of the resulting filtrate cake; (iii) removal of remaining impurities by single or stepwise adsorption onto hcCaSiO$_3$; and, (iv) subsequent alcoholic (e.g., ethanol) precipitation of the purified plasmid DNA which affords a stable bulk product from which concentrated formulation solutions can be readily prepared.

Another embodiment of the present invention which relies on additional steps beyond the core process includes an upstream step of cell lysis, which may be performed by any number of processes now available to the skilled artisan. Therefore, combination of process steps may include an upstream cell lysis step to include, for example the following process: (i) cell lysis; (ii) lysate clarification as discussed herein, (iii) single or stepwise precipitation of plasmid DNA with a detergent, such as CTAB; (iv) selective dissolution of plasmid with salt solution; (v) removal of remaining impurities by single or stepwise adsorption onto hcCaSiO$_3$; and, (vi) subsequent alcohol (e.g. ethanolic) precipitation of the purified plasmid DNA which affords a stable bulk product from which concentrated formulation solutions can be readily prepared. Any known methods of cell lysis are contemplated for this upstream step. Preferred cell lysis methodology is disclosed herein.

An additional embodiment of the present invention relates to a process whereby an additional step of lysate clarification is combined with the core process steps, cell lysis and a salt dissolution step, resulting in the following stepwise process including but not limited to the steps of (i) cell lysis; (ii) lysate clarification, preferably with diatomaceous earth-aided filtration or centrifugation; (iii) selective precipitation of plasmid DNA with a detergent, such as CTAB; (iv) selective dissolution of the plasmid DNA with salt solution; (v) adsorption of residual impurities onto hcCaSiO$_3$; and (vi) precipitation of purified plasmid DNA using alcohol (such as ethanol). Alternatives to the use of CTAB for plasmid precipitation, alcoholic precipitation, and clarification materials are discussed herein.

The methods of the present invention allow for clinical grade DNA plasmid purification from microbial cells including but not limited to bacterial cells, plant cells, yeast, baculovirus, with E. coli being the preferred micorbial host. The clinical grade plasmid DNA purified by the methods described herein is extremely useful for administration to humans as a vaccine or gene therapy vehicle.

The present invention relates to large scale methodology which represents inexpensive manufacturing alternatives for production clinical-grade plasmid DNA. The essence of the invention centers around several downstream processing steps which include (i) stepwise precipitation of plasmid DNA with CTAB; (ii) selective dissolution of plasmid with salt solution; (iii) removal of remaining impurities by adsorption onto crystallized calcium silicate; followed by concentration of the final product. The core of the present invention comprises the above steps in a scalable design process to generate DNA plasmid preparations suitable for human administration.

The present invention relates to methods of isolating clinical-grade plasmid DNA from microbial cells. The plasmid purification methods of the present invention are based in part on operations including, but not necessarily limited to: (i) cell lysis; (ii) lysate clarification with diatomaceous earth-aided filtration; (iii) stepwise precipitation of plasmid DNA with CTAB in the presence of a useful amount of diatomaceous earth; (iv) selective dissolution of the CTAB pellet with a salt solution; (v) removal of remaining impurities by adsorption onto crystallized calcium silicate; and, (vi) subsequent alcoholic precipitation of the purified plasmid DNA which affords a stable bulk product from which concentrated formulation solutions can be readily prepared.

In a preferred aspect of the invention, large scale plasmid preparation involves several downstream processing steps which include (i) stepwise precipitation of plasmid DNA with CTAB; (ii) selective dissolution of plasmid with salt solution; (iii) removal of remaining impurities by adsorption onto crystallized calcium silicate; and, (iv) preferably, the subsequent alcohol (such as an ethanolic) precipitation of the purified plasmid DNA which affords a stable bulk product from which concentrated formulation solutions can be readily prepared. It will be known to the skilled artisan that aspects of the design process are interchangeable, including step (iv), as disclosed herein.

In another preferred embodiment of the present invention, cell lysis is followed by filtration with diatomaceous earth in an amount which effectively clarifies the cell lysate. This initial step is followed at least by the additional downstream steps, as noted above; namely (i) stepwise precipitation of plasmid DNA with CTAB; (ii) selective dissolution of plasmid with salt solution; (iii) removal of remaining impurities by adsorption onto crystallized calcium silicate; and, (iv) preferably, an ethanolic precipitation of the purified plasmid DNA.

In another preferred embodiment of the present invention, complete cell lysis prior to lysate clarification involves transfer of cells harvested from the fermentation broth or the fermentation broth directly either with or without lysozyme treatment, preferably with a lysozyme treatment, through a heat exchange apparatus as disclosed in PCT International Application Nos. PCT/US95/09749 (WO96/02658) and PCT/US96/07083 (WO96/36706). This lysis step is followed by inclusion of the following steps subsequent to cell lysis, including but not limited to (i) a selective two-step precipitation of plasmid DNA using a cationic detergent, preferably CTAB; (ii) selective dissolution of plasmid with a salt solution; (iii) adsorption of residual impurities onto calcium silicate hydrate; and (iv) precipitation of purified plasmid DNA using an alcohol (including but not limited to ethanol, methanol or isopropanol) prior to final formulation of the clinical grade plasmid preparation. To this end, this aspect of the invention relates to a method for the purification of supercoiled plasmid DNA from a microbial fermentation, which comprises (a) harvesting microbial cells from a fermentation broth; (b) resuspending the harvested cells in a standard STET buffer and adding to the harvested microbial cells a sufficient amount of a lysis solution; (c) heating the microbial cells of step b) to a temperature between from about 60° C. to about 70° C. up to about 100° C. in a flow-through heat exchanger to form a cell lysate; (d) cooling the cell lysate; (e) clarifying the cell lysate using filtration with diatomaceous earth; (f) precipitating residual cell debris and impurities with a first cetyltrimethylammonium-induced precipitation; (g) selectively precipitating supercoiled plasmid DNA with a second cetyltrimethylammonium-induced precipitation; (h) redissolving the supercoiled plasmid DNA in a well defined buffer of optimized ionic strength and salt composition; (i) adsorbing residual impurities onto calcium silicate within the buffer of step (h); (j) precipitating supercoiled plasmid DNA with ethanol; (k) filtering to collect and wash the precipitate; (l) drying to remove ethanol; (m) redissolving purified supercoiled plasmid DNA in a physiologically acceptable formulation buffer; and, (n) sterilizing by filtration through a 0.22 μm filter. It is also within the scope of this portion of the invention to omit steps (j)-(n) while washing and sterilizing the buffer of step (i), followed by DNA concentration by ethanol precipitation, resulting in a powder precipitate containing the supercoiled plasmid DNA. As described herein, the first and second CTAB-induced precipitation steps (via a 1% w/v CTAB feed in a standard STET buffer) may effectively range from about 0.25% to about 0.28% first cut and from about 30% to about 0.33% for a second cut. It is again noted that it is within the purview of the skilled artisan, with this specification in hand, to alter stepwise precipitation ranges to adjust to any peculiarities of various buffer systems, such that a workable amount of impurities are first precipitated away from the remaining buffer solution comprising supercoiled plasmid DNA, which is then precipitated with an additional CTAB-induced precipitation. Components such as EDTA and/or Triton-based detergents, as discussed herein, may be added, being useful at biologically effective concentrations within the various buffers to help promote precipitation of plasmid DNA.

In another preferred embodiment of the present invention, complete cell lysis prior to lysate clarification involves transfer of cells harvested from the fermentation broth or the fermentation broth directly either with or without lysozyme, preferably in the presence of lysozyme, through a heat exchange apparatus as disclosed in PCT International Application Nos. PCT/US95/09749 (WO96/02658) and PCT/US96/07083 (WO96/36706). This cell lysis procedure initiates the protocol which includes but is not limited to (i) lysate clarification with diatomaceous earth-aided filtration; (ii) a selective one step precipitation of plasmid DNA using a cationic detergent, preferably CTAB; (iii) selective dissolution of plasmid with a salt solution; (iv) adsorption of residual impurities onto calcium silicate hydrate; and (v) precipitation of purified plasmid DNA using an alcohol, prior to final formulation of the clinical grade plasmid preparation. To this end, this aspect of the invention relates to a method for the purification of supercoiled plasmid DNA from a cell lysate of a large scale microbial fermentation, which comprises: (a) harvesting microbial cells from a fermentation broth; (b) resuspending the harvested cells in a standard STET buffer and adding to the harvested microbial cells a sufficient amount of a lysis solution; (c) heating the microbial cells of step b) to a temperature between 60° C. and 70° C. to up to about 100° C. in a flow-through heat exchanger to form a cell lysate; (d) cooling the cell lysate; (e) clarifying the cell lysate using filtration with diatomaceous earth; (f) precipitating supercoiled plasmid DNA with cetyltrimethylammonium; (g) redissolving the supercoiled plasmid DNA in a well defined buffer of optimized ionic strength and salt composition; (h) adsorbing residual impurities onto calcium silicate within the buffer of step (g); (i) precipitating supercoiled plasmid DNA with ethanol; (j) filtering to collect and wash the precipitate; (k) drying to remove ethanol; (l) redissolving purified supercoiled plasmid DNA in a physiologically acceptable formulation buffer; and, (m) sterilizing by filtration through a 0.22 µm filter. It is also within the scope of this portion of the invention to omit steps (i)-(m) while washing and sterilizing the buffer of step (h), followed by DNA concentration by ethanol precipitation, resulting in a powder precipitate containing the supercoiled plasmid DNA. A preferred lysis temperature of step (b) is from about 70° C. to about 80° C., while a single CTAB cut may preferably be at a CTAB concentration from about 0.30% to about 0.33% (via a 1% w/v CTAB feed in a standard STET buffer), again possibly being influenced by buffer conditions. Buffer components such as EDTA and Triton are, as noted elsewhere, available for addition to buffers to enhance plasmid DNA recovery.

In yet another preferred embodiment, cell lysis is carried out by modification of the techniques as described by Bimboim & Doly (1979, *Nucleic Acid Res.* 7: 1513-1523), the modification wherein cells are lysed using dilute sodium hydroxide followed by KOAc neutralization. This cell lysis step is then followed by inclusion of the following steps subsequent to cell lysis, including but not limited to (i) lysate clarification with diatomaceous earth-aided filtration, (ii) selective precipitation of plasmid DNA using a cationic detergent, preferably CTAB, (iii) selective dissolution of plasmid with a salt solution and (iv) adsorption of residual impurities onto calcium silicate hydrate prior to final formulation of the clinical grade plasmid preparation. To this end, an aspect of this portion of the invention relates to a method for the purification of supercoiled plasmid DNA from a cell lysate of a large scale microbial fermentation, which comprises: (a) harvesting microbial cells from a fermentation broth; (b) resuspending the harvested cells in a standard STET buffer and adding to the harvested microbial cells a sufficient amount of lysozyme/alkaline/KOAc to promote cell lysis, forming a cell lysate; (c) clarifying the cell lysate using filtration with diatomaceous earth; (d) precipitating residual cell debris and impurities with a first cetyltrimethylammonium-induced precipitation; (e) selectively precipitating supercoiled plasmid DNA with a second cetyltrimethylammonium-induced precipitation; (f) redissolving the supercoiled plasmid DNA in a well defined buffer of optimized ionic strength and salt composition; (g) adsorbing residual impurities onto calcium silicate with the buffer of step (f); (h) precipitating supercoiled plasmid DNA with ethanol; (i) filtering to collect and wash the precipitate; (j) drying to remove ethanol; (k) redissolving purified supercoiled plasmid DNA in a physiologically acceptable formulation buffer; and, (l) sterilizing by filtration through a 0.22 µm filter. It is also within the scope of this portion of the invention to omit steps (j)-(n) while washing and sterilizing the buffer of step (i), followed by DNA concentration by ethanol precipitation, resulting in a powder precipitate containing the supercoiled plasmid DNA. As described herein, the first and second CTAB-induced precipitation steps (via a 1% w/v CTAB feed in a standard STET buffer) may effectively range from about 0.25% to about 0.28% first cut and from about 30% to about 0.33% for a second cut. It is again noted that it is within the purview of the skilled artisan, with this specification in hand, to alter stepwise precipitation ranges to adjust to any peculiarities of various buffer systems, such that a workable amount of impurities are first precipitated away from the remaining buffer solution comprising supercoiled plasmid DNA, which is then precipitated with an additional CTAB-induced precipitation. Buffer components such as EDTA and/or Triton-based detergents may be added, such components being useful at biologically effective concentrations within the various buffers to help promote precipitation of plasmid DNA.

In another preferred embodiment, cell lysis is carried out by the modified Bimboim & Doly method, where, as noted above, cells are lysed using dilute sodium hydroxide followed by KOAc neutralization. This cell lysis step is then followed by inclusion of the following steps subsequent to cell lysis, including but not limited to (i) lysate clarification with diatomaceous earth-aided filtration, (ii) selective precipitation of plasmid DNA using a cationic detergent, preferably CTAB, (iii) selective dissolution of plasmid with a salt solution and (iv) adsorption of residual impurities onto calcium silicate hydrate, and (v) precipitation of purified plasmid DNA using ethanol, prior to final formulation of the clinical grade plasmid preparation. An aspect of this portion of the invention relates to a method for the purification of supercoiled plasmid DNA from a cell lysate of a large scale microbial fermentation, which comprises (a) harvesting microbial cells from a large scale fermentation; (b) resuspending the harvested cells in a standard STET buffer and adding to the harvested microbial cells a sufficient amount of lysozyme/alkaline/KOAc to promote cell lysis, forming a cell lysate; (c) clarifying the cell lysate using filtration with diatomaceous earth; (d) precipitating supercoiled plasmid DNA with cetyltrimethylammonium; (e) redissolving the supercoiled plasmid DNA in a well defined buffer of optimized ionic strength and salt composition; (f) adsorbing residual impurities onto hydrated, crystallized calcium silicate; (h) precipitating supercoiled plasmid DNA with ethanol; (i) filtering to collect and wash the precipitate; (j) drying to remove ethanol; (k) redissolving purified supercoiled plasmid DNA in a physiologically acceptable formulation buffer; and, (l) sterilizing by filtration through a 0.22 μm filter. It is also within the scope of this portion of the invention to omit steps (i)-(m) while washing and sterilizing the buffer of step (h), followed by DNA concentration by ethanol precipitation, resulting in a powder precipitate containing the supercoiled plasmid DNA. A preferred lysis temperature of step (b) is from about 70° C. to about 80° C., while a single CTAB cut (via a 1% w/v CTAB feed in a standard STET buffer) may preferably be at a CTAB concentration from about 0.30% to about 0.33%, again possibly being influenced by buffer conditions. Buffer components such as EDTA and Triton are, as noted elsewhere, available for addition to buffers to enhance plasmid DNA recovery.

The harvested microbial cells are dissolved in STET buffer and lysozyme is added as described above. It is readily apparent to those skilled in the art that modifications of this basic buffer formula can be made and are suitable for use in the present invention. Modifications to this basic buffer formula that do not substantially affect or alter the outcome of the present process are intended to be within the scope of the process of the present invention. However, in a preferred embodiment of the present invention, the selective precipitation of plasmid DNA with CTAB as described throughout this specification is carried out in the presence of a physiologically acceptable buffer which comprises a chelator which effectively removes divalent cations such as $Mg^{++}$ and $Ca^{++}$. Magnesium is an essential cofactor for DNAse and calcium complexes with plasmid DNA, preventing precipitation by CTAB. It is exemplified herein and preferred that the chelator be EDTA. However, any chelator which removes divalent cations such as $Mg^{++}$ and $Ca^{++}$ may be added to the buffers utilized to practice the plasmid DNA purification methods disclosed herein. It has been shown by the inventors that EDTA concentrations of 1 mM, 5 mM, 10 mM and 100 mM are effective in promoting CTAB-induced plasmid DNA precipitation. Therefore, any physiologically acceptable concentration of a chelator of choice, including EDTA, which promotes CTAB-induced plasmid DNA precipitation may be utilized through the initial step-wise plasmid DNA precipitation steps.

Diatomaceous earth (DE) is a loosely coherent powdery material formed almost entirely from the shell fragment of hydrous diatoms. Usually fine in texture and gray or white in color, diatomaceous earth is composed largely of silicon dioxide or silica in its pure form, having a silica content as high as 94%. Diatomaceous earth is available commercially in three forms: natural, calcinated and flux-calcinated. The calcinated form of DE is generated by calcification at high temperatures whereas flux-calcinated DE is prepared by calcination in the presence of flux, such as soda ash or sodium chloride. Diatomaceous earth is available from multiple commercial sources and any and all available forms are contemplated for use in practicing the methods of the present invention, including but not limited to Celpure 65, Celpure 100, Celpure 300, Celpure 100, and LRA™ (all from Advanced Minerals), as well as Cellulosic filter aids such as Solka Floc. As noted above and exemplified herein, clarification of the cell lysate via diatomaceous earth-aided filtration is a preferred downstream processing step since this step appears to be more scalable and the plasmid DNA less prone to shear effects of large scale centrifugation. However, other alternatives may be utilized to remove host cell debris and genomic DNA, such as centrifugation.

In an especially preferred embodiment of the present invention, the selective precipitation of plasmid DNA with CTAB described throughout this specification is accomplished in a stepwise fashion, selectively precipitating cell debris, GDNA and some DNA degradates at a low cut CTAB concentration, followed by a second high cut CTAB-induced precipitation of plasmid DNA. While CTAB is preferred for stepwise, selective precipitation of plasmid DNA, other compounds which may be useful include but are not limited to C16: cetyltrimethylammonium chloride; C16: cetyldimethylethylammonium bromide or chloride; C16: cetylpyridinium bromide or chloride; C14: tetradecyltrimethylammonium bromide or chloride; C12: dodecyltrimethylammoniumbromide or chloride; C12: dodecyldimethyl-2 phenoxyethylammonium bromide; C16: Hexadecylamine: chloride or bromide salt; C16: hexadecylpyridinium bromide or chloride; and, C12 Dodecyl amine or chloride salt. It will be within the purview of the artisan to test potential substitutes for the detergent exemplified herein to identify a compound which effectively precipitates supercoiled plasmid DNA away from the various cell lysate impurities.

In another embodiment of the present invention, downstream batch adsorption of impurities is carried out in the presence of a hydrated calcium silicate ($hcCaSiO_3$), such as the synthetic hydrated calcium silicate LRA™ (Advanced Minerals Corporation, Lompoc, Calif. 93438). It is also possible to substitute column mode adsorption for the hydrated calcium silicate ($hcCaSiO_3$) adsorption step. For example, if using LRA™, first perform a settle decant to remove LRA™ fines followed by packing the LRA™ into a column. Ten column volumes of NaCl (at the same NaCl concentration as the plasmid feed solution) are applied to the column, followed by application of the plasmid solution. Supercoiled plasmid DNA is the first form of DNA to elute in the effluent. Later fractions will contain plasmid degradates and genomic DNA. Endotoxin and CTAB are also eliminated by being tightly bound to the column. Fractions that contain nucleic acid impurities are not pooled. A hydrated calcium silicate material is described in PCT International Application PCT/US96/20034 (WO 98/01464), which is hereby incorporated by reference. As pointed out in WO 98/01464, many methods are known in the art for the preparation of $hcCaSiO_3$ compounds (e.g., see Taylor, 1964, Ed., *The Chemistry of Cements*, Academic Press. As further noted in WO 98/01464, the particle size of $hcCaSiO_3$ may be from about 0.01 micron to about 0.10 micron, as determined by known methods, such as x-ray measurement and/or electron microscopy. Of these small particles, aggregates as large as about 100 microns may be present. As noted below, a preferred embodiment shows the $hcCaSiO_3$ with a retention on a 325 mesh sieve as less than about 10% by weight, more preferably less than about 8% by weight. In many embodiments which are preferred, the $hcCaSiO_3$ is in powder form with a surface area of greater than about 75 $m^2/g$, and preferably between from about 75 $m^2/g$ to about 200 $m^2/g$. A preferred hydrated calcium silicate material utilized herein is a fine powder prepared by hydrothermal reaction of diatomaceous earth, hydrated calcium oxide (calcium hydroxide) and water. The final product is in a crystalline form which comprises about 47% silicon ($SiO_2$) by weight, a stoichiometric amount of calcium (CaO) at about 32% by weight, about 2.5% aluminum by weight ($Al_2O_3$), about 1.2% combined sodium ($Na_2O$) and potassium ($K_2O$) by weight; about 0.7% iron by weight (reported as $Fe_2O_3$); about 0.6% magnesium by weight (MgO), with the remainder (about 16.6% $H_2O$). This preferred form possesses a retention on a 325 mesh sieve of about 6% by weight and a surface area of about 120 $m^2/g$ (as determined using the B.E.T. method). The percentage by weight ranges of the above-identified components of $CaSiO_3$ may include but are not necessarily limited to: $SiO_2$ (45-95%); CaO (5-35%); $H_2O$ (1-20%), and in some instances from about 1% to about 10% of various impurities, including but not necessarily limited to $Al_2O_3$, alkali metals such as sodium ($Na_2O$) and potassium ($K_2O$) oxides, iron oxide ($Fe_2O_3$) and magnesium oxide (MgO), as well as small amounts of soluble aluminum. It will be within the purview of the skilled artisan to substitute alternative forms of hydrated calcium-based materials for use in the adsorption step which may selectively bind larger DNA fragments as exemplified with LRA™, Matrex™ (Amicon), and hydroxyapetite [calcium (dibasic) phosphate]. Regardless, a synthetic hydrated calcium silicate with characteristics similar to LRA™ (as disclosed in PCT/US96/20034) is a preferred adsorbent material to remove residual DNA degradates such as open relaxed and linear forms, host DNA and RNA, endotoxin, proteins and clearance of detergent additives such as CTAB.

Therefore, the methods described herein result in achieving separation between various forms of plasmid (supercoiled plasmid DNA [the intended product for use as a DNA vaccine or gene therapy vehicle], open relaxed plasmid DNA, linear plasmid DNA and plasmid DNA concatomers) and to remove host contaminants such as LPS (endotoxin), gRNA, gDNA and residual proteins.

The plasmid to be isolated and purified by the process of the present invention can be any extrachromosomal DNA molecule. The plasmids can be high copy number per cell or low copy number per cell. The plasmids can also be of virtually any size. It is readily apparent to those skilled in the art that virtually any plasmid in the microbial cells can be isolated by the process of the present invention.

The process of the present invention is suitable for use with microbial fermentations in general. It is readily apparent to those skilled in the art that a wide variety of microbial cells are suitable for use in the process of the present invention, including but not limited to, bacterial cells, plant cells, fungal cells including yeast, and baculovirus. A preferred microbial fermentation is a bacterial fermentation of cells containing the plasmid to be isolated and purified. A preferred bacterial fermentation is a fermentation of E. coli containing the plasmid to be isolated and purified. It is readily apparent to those skilled in the art that bacterial fermentations other than E. coli fermentations are suitable for use in the present invention. The large scale microbial fermentations of the present invention may be grown in any liquid medium which is suitable for growth of the bacteria being utilized. While the disclosed methodology is applicable to smaller fermentation volumes, an especially useful aspect of the present invention is scaleability to large scale microbial cell fermentations. The term "large scale" as used herein is considered to be total cell fermentation volumes of greater than about 5 liters, or the cells harvested from a fermentation volume greater than about 5 liters. The large scale fermentation methodology of the present invention is applicable to clinical size lots which represent, but are not limited to, approximately 100-200 liter fermentations.

One embodiment of the present invention which comprises each of these above-identified steps consists of the following steps: (i) tangential flow filtration of fermentation broth to concentrate and diafilter cells containing plasmid DNA; (ii) resuspension of cells, (iii) 37° C. incubation of cell slurry with recombinant lysozyme, (iv) cell lysis via rapid heating, followed by cooling of lysate, (vi) clarification of lysate using filtration with diatomaceous earth, (v) precipitation of residual cell debris and impurities such as genomic DNA with the addition of CTAB, (vi) selective precipitation of plasmid DNA with CTAB, (vii) selective redissolution of plasmid DNA, (viii) batch adsorption of residual endotoxin and CTAB onto calcium silicate, (ix) batch adsorption of residual protein, nucleic acid, and other impurities onto calcium silicate, (x) precipitation of plasmid DNA with ethanol, (xi) filtration to collect and wash the precipitate; (xii) vacuum drying to remove ethanol; (xii) redissolution of purified plasmid DNA in formulation buffer; and (xiii) 0.22 μm sterile filtration.

In another embodiment of the present invention, unharvested cells from the fermentation broth are incubated with lysozyme at 37° C. for approximately 1 hour and the cell slurry is pumped through a heat exchanger which achieves an exit temperature of 75-80° C. This is followed by pumping through a second heat exchanger to cool the lysate to 20-25° C. The lysate material is subjected to (i) clarification of lysate using filtration with diatomaceous earth, (ii) precipitation of residual cell debris and impurities such as genomic DNA with the addition of CTAB, (iii) selective precipitation of plasmid DNA with CTAB, (iv) selective dissolution of plasmid DNA, (v) batch adsorption of residual endotoxin and CTAB onto calcium silicate, (vi) batch adsorption of residual protein, nucleic acid, and other impurities onto calcium silicate, (vii) precipitation of plasmid DNA with ethanol, (viii) filtration to collect and wash the precipitate; (ix) vacuum drying to remove ethanol; (x) dissolution of purified plasmid DNA in formulation buffer; and (xi) 0.22 μm sterile filtration.

Microbial cells containing the plasmid are harvested from the fermentation medium to provide a cell paste, or slurry. Any conventional means to harvest cells from a liquid medium is suitable, including, but not limited to centrifugation or microfiltration. A cell paste is generated by harvesting microbial cells containing the plasmid DNA from the fermentation broth. The harvest consists of (i) concentrating the cells by a factor of four using tangential flow filtration across a 500 kDa nominal molecular weight A/G Tech membrane and (ii) diafiltering the concentrated cells with three equivalent volumes of sterilized, 120 mM saline. The harvested cells are resuspended in sterilized STET buffer (8% w/v sucrose, 50 mM Tris-HCl, 100 mM EDTA, 2% v/v Triton X-100, pH 8.5) to a dilution corresponding to an optical density of 30 at 600 nm. The suspension is heated to 37° C. and Ready-Lyse™ lysozyme from Epicentre Technologies is added to a concentration of 500 kU/L. After 45 minutes at 37° C., the cell slurry is pumped through a heat transfer coil submerged in boiling water so that its temperature reaches 70° C. upon exiting the coil. The lysate is then cooled to approximately 20° C. by flowing through a heat transfer coil submerged in an ice water bath. The lysis step comprising transfer of the cell slurry through a heat exchange apparatus is disclosed in PCT International Application Nos. PCT/US95/09749 (WO96/02658) and PCT/US96/07083 (WO96/36706), herein incorporated by reference. Briefly, the harvested microbial cells are resuspended in STET buffer and lysozyme is added as described above. It is readily apparent to those skilled in the art that modifications of this basic buffer formula can be made and are suitable for use in the present invention. Modifications to this basic buffer formula that do not substantially affect or alter the outcome of the present process are intended to be within the scope of the process of the present invention. However, it is especially preferred that this step take place in the presence of a physiologically acceptable buffer comprising a chelator which effectively removes divalent cations such as $Mg^{++}$ and $Ca^{++}$, such as EDTA. As noted above, any chelator concentration which promotes CTAB-induced plasmid DNA precipitation may be used, which has been exemplified over a wide concentration range from about 1 mM to greater than 100 mM EDTA. These EDTA concentration ranges result in optimal CTAB-induced precipitation of supercoiled plasmid DNA while also inhibiting DNAse activity. The buffer pH range may be adjusted according to the best results provided for the particular strain of bacteria being used. The preferred pH range is about 8.0-8.5. The suspension is then heated to about 60-100° C., with about 70-80° C. preferred, in a flow-through heat exchanger. This is followed by cooling to 20-25° C. in a second heat exchanger. An alternative lysis method of Birnboim and Doly (1979, *Nucleic Acid Res.* 7: 1513-1523) is also contemplated. In this method, cells are lysed using dilute sodium hydroxide followed by KOAc neutralization. SDS is omitted from the alkaline step to prevent interference with CTAB-induced DNA precipitation. Lysis yield was not affected by the deletion of SDS.

Diatomaceous earth (Celpure™; Advanced Minerals) is then added to the cooled lysate at a concentration of 30 g/L. The resulting slurry is filtered, and the cake is washed to recover product liquid. Celpure™ is then mixed into the clarified lysate at roughly 10 g/L. A range of Celpure™ from about 5 g/L -15 g/L at this step is preferred. Residual, finely divided cell debris and other impurities, including genomic DNA and relaxed circular and linear DNA degradates are precipitated from the clarified lysate by adding a solution of 1.0% w/v CTAB in 40 mM NaCl to a final concentration of 0.1-0.3% % w/v CTAB. The resulting slurry is filtered, after providing initial recirculation until its turbidity is less than 10 NTU. Celpure™ is added to the filtrate at a body feed concentration of approximately 10 g/L. This provides a matrix onto which plasmid DNA precipitates upon increasing the CTAB concentration to 0.25%-0.45% w/v using 1.0% w/v CTAB in 40 mM NaCl. The slurry is filtered, and the filtrate is recirculated until its turbidity is less than 10 NTU. In Example 1, the resulting plasmid DNA-impregnated filter cake was washed with 0.30-0.33% w/v CTAB in 40 mM NaCl. The artisan of ordinary skill will realize the low and high cut CTAB ranges may be manipulated depending upon variations in plasmid DNA concentration, ionic strength and/or temperature. The filter cake is then dissolved in about 0.2M to about 2.0 M NaCl with 100 mM Tris (pH 8.2). Plasmid DNA redissolves as NaCl exchanges with CTAB. Again, the skilled artisan may choose various salt concentrations to wash and/or redissolve the filter cake. The suspension is filtered over a stainless steel membrane to remove Celpure™, after providing initial recirculation to achieve low turbidity. The filtrate is subjected to two batch adsorption steps using $hcCaSiO_3$ (e.g., LRA™ from Advanced Minerals). The first adsorption step removes residual endotoxin and CTAB; the second removes residual proteins, relaxed circular and linear DNA degradates as well as host DNA and RNA. LRA™ is added at 45 grams per gram of DNA in the first adsorption step. The resulting slurry is incubated at 20° C. for one hour and filtered. The filter cake is washed with 1.2M NaCl, or a reasonable salt concentration, as noted above. Fresh LRA™ is added to the filtrate and wash solution at 50 grams per gram of DNA, and the resulting slurry is incubated at 20° C. for roughly five hours. The slurry is then filtered to remove LRA™, and the resulting filter cake is washed with 1.2M NaCl. It will be evident to the artisan of ordinary skill in the art that the above batch adsorption steps may be carried out whereby the calcium silicate is slurried into solution containing the reconstituted CTAB precipitate, or the batch adsorption steps may be completed using a packed column comprising $hcCaSiO_3$, as noted above in reference to use of a $hcCaSiO_3$ column for use in treating the dissolved CTAB intermediate. One equivalent volume of absolute ethanol is added to the filtrate and wash from the second $hcCaSiO_3$ step to precipitate the purified plasmid DNA. The resulting precipitate is recovered via filtration and washed immediately with absolute ethanol. The washed precipitate is dried by vacuum at 20° C. to remove ethanol and is subsequently stored at 4° C. until reformulation. Upon reformulation in a buffer suitable for injection, the purified plasmid DNA solution is subjected to a 0.22 μm sterile filtration. Alternatively, the bulk product powder may be isolated from the ethanolic precipitate if a precipitate forms an unfilterable paste. The precipitated paste is centrifuged and the paste is added to 100% EtOH which is mixed with a high speed homogenizer such as a rotor stator. The paste is simultaneously dehydrated and wet milled into hard particles. These particles are amenable to filtration and drying.

As noted above, instead of precipitating a bulk powder, the purified plasmid DNA preparation may be transferred into a pharmaceutically acceptable carrier or buffer solution. Pharmaceutically acceptable carriers or buffer solutions are known in the art and include those described in a variety of texts such as Remington's Pharmaceutical Sciences. Any method suitable for concentrating a DNA sample is suitable for use in the present invention. Such methods includes ultrafiltration, alcohol precipitation, lyophilyzation and the like, with ethanol purification being preferred. The purified plasmid preparation may be sterilized by any method of sterilization which does not affect the utility of the DNA product, such as sterilization by passage through a membrane having a sufficiently small pore size, for example 0.22 microns and smaller.

The final product contains calcium which is shed from a loosely bound state on $hcCaSiO_3$. A typical preparation might have about 1.6% w/w in the precipitated product. For preparation of clinical formulations, the residual calcium can be removed by conventional methods involving EDTA. For example, complexation of calcium by addition of EDTA can be performed in conjunction with either ultrafiltration or precipitation and the calcium-EDTA complex flushed out with the precipitation liquors or ultrafiltration permeate streams. Alternately, a small chelating column containing EDTA would more efficiently remove the calcium without introducing EDTA into the process stream.

The methods of the present invention allow for clinical grade DNA plasmid purification from organisms including but in no way limited to yeast and *E. coli*. The clinical grade plasmid DNA purified by the methods described herein is extremely useful for administration to humans as a vaccine or gene therapy vehicle.

The following examples are provided to illustrate the process of the present invention without, however, limiting the same thereto.

EXAMPLE 1

Purification of Plasmid DNA

The following protocol for the purification of plasmid DNA from *E. coli* resulted in the isolation of approximately 730 mg of purified, supercoiled plasmid DNA. A schematic of the core plasmid purification process disclosed herein is shown in FIG. 1.

Cell lysis—600 mL of cell paste was thawed using warm tap water and resuspended in 5.4 L of STET buffer. The 10-fold dilution yielded a slurry with an optical density of 30 at 600 nm. 40 mcL of Ready-Lyse Lysozyme (Epicentre, 30 kU/mcL) was then added to the cell slurry. The temperature of the diluted cell slurry was raised to approximately 40° C. After 45 minutes of mixing, the cells were heat-lysed through an electro-polished, stainless steel coil immersed in a boiling water bath. The flow rate was adjusted so that the temperature of fluid exiting the heat exchanger was roughly 70° C. The lysis coil was then cleaned with pyrogen-free water, immersed in an ice water bath, and used to cool the hot lysate to 30° C. Lysate was cooled within 30 min of the completion of heat lysis. The total lysate volume was 5.6 L.

Clarification—Celpure P300 (Advanced Minerals) at a body feed concentration of 30 g/L was used to clarify the cooled lysate. Celpure P300 was mixed into the lysate, and the resulting slurry was divided into four portions. The amount of Celpure can be varied over a wide range depending upon the final scale of operation, the desired filter size and configuration and the designed production rate of the manufacturing facility. Similar considerations dictate the quantities of diatomaceous earth in the low cut and high cut filtration steps described herein. Each portion was filtered separately through a 25-micron stainless steel mesh contained within a 6-inch diameter filter housing. The filtrate was initially recirculated until its turbidity decreased to approximately 10 NTU. Following each filtration, pressurized air was used to displace interstitial fluid within the filter cake. The total volume of clarified lysate was 5.05 L. The total DNA concentration and purity of supercoiled plasmid DNA, as measured by an analytical HPLC assay, were 0.338 g/L and 83.6%, respectively.

CTAB Probe—A rapid CTAB probe was employed to determine the approximate low and high cut CTAB concentrations. Incremental amounts of 1.0% w/v CTAB in 40 mM NaCl were added to 500 mcL aliquots of clarified lysate in 1.5 mL glass vials. Vials were vortexed and visually inspected for the presence of DNA precipitates. Based on the probe results, low and high cut CTAB concentrations of 0.23 and 0.30% w/v, respectively, were assigned.

Low cut CTAB step—To 5.05 L of clarified lysate a 1.5 L solution of 1.0% w/v CTAB in 40 mM NaCl was added at room temperature over a 43 minute time period. 34.2 g of Celpure 300 was then added. The slurry was then filtered through a 25-micron stainless steel mesh contained within a 6-inch diameter filter housing. Filtrate was initially recirculated until its turbidity was constant. The filter cake was not washed but was dried using pressurized air. The final volume of product-containing filtrate was 6.44 L.

Figure 2:
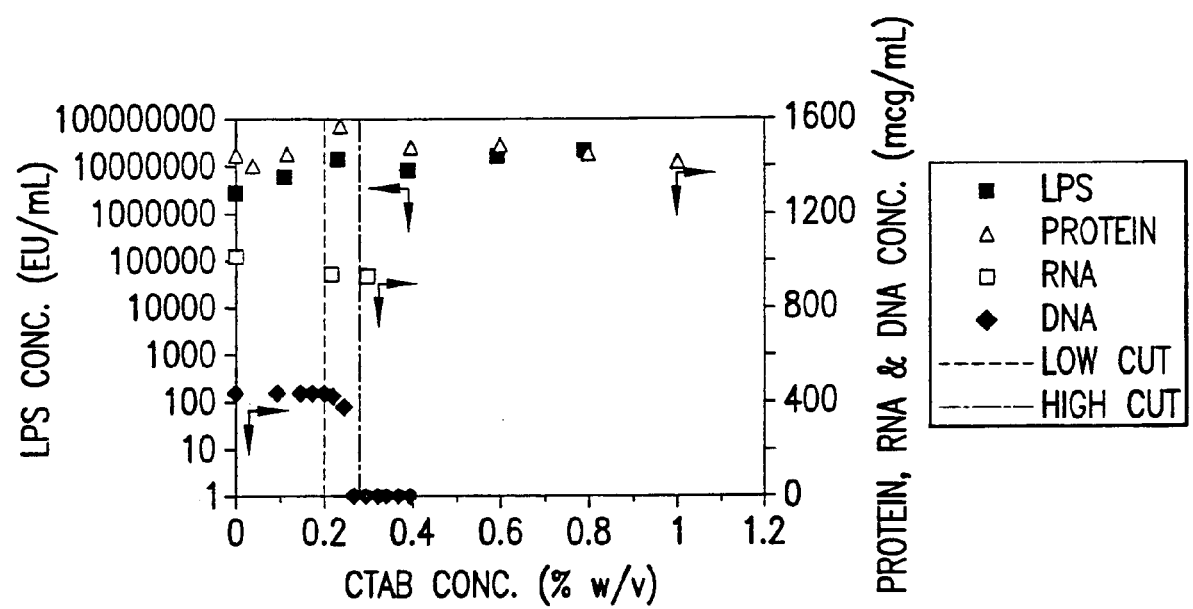
FIG. 2 shows a concentration profile during step precipitation with CTAB. Plasmid DNA is precipitated over a tight detergent increment. The step is selective for removal of protein, RNA and endotoxin which remain soluble.

High cut CTAB step—29.3 g of Celpure P300 was added to the low cut filtrate. With agitation, 650 mL of 1.0% w/v CTAB in 40 mM NaCl was then added to the slurry over a time period of roughly 30 min. Analytical HPLC analyses revealed that all of the DNA had precipitated. The high cut slurry was then filtered through a 25-micron stainless steel mesh contained within a 6-inch diameter filter housing. The filtrate was recirculated until a constant turbidity was observed. The filter cake was washed with a 1 L solution of 0.3% w/v CTAB in 12 mM NaCl after the filtration of the high cut slurry was completed. Two 500 mL wash fractions were collected. The washed cake was then partially dried using pressurized air, collected from the filter housing, and weighed to determine the mass of residual liquid within the cake. The total mass of cake was 113 g. Celpure and precipitated DNA contributed approximately 29 and 2 g, respectively, indicating that there was roughly 82 mL of residual liquid in the washed cake. FIG. 2 shows a concentration profile during step precipitation with CTAB. These data show that plasmid DNA precipitates over a tight detergent increment. This CTAB-precipitation step is selective for removal of protein, RNA and endotoxin, which remain soluble.

Selective redissolution of washed, high cut cake—700 mL of sterile water was added to the washed, high cut cake, bringing the total volume of liquid to approximately 782 mL. Roughly 86 mL of 5 M NaCl was added to the slurry, yielding a NaCl concentration of approximately 0.5 M and redissolving the supercoiled plasmid DNA. Residual diatomaceous earth was filtered through a 25-micron stainless steel mesh contained within a 6-inch diameter filter housing to separate the Celpure from the redissolved supercoiled plasmid DNA. The filtrate was recirculated until a clear filtrate was obtained. The filter cake was washed with approximately 1 L of 0.5 M NaCl to recover interstitial, product-containing liquid. The 0.5 M NaCl wash was collected in four fractions. An analytical HPLC assay was used to assay the product filtrate and the four wash fractions for total DNA concentration and supercoiled plasmid DNA purity. The volume, total DNA concentration, and composition of supercoiled DNA of the product filtrate and 0.5 M NaCl washes were the following: (i) product filtrate: 800 mL, 1.933 g/L, 93.0%, (ii) wash fraction 1: 200 mL, 0.203 g/L, 89.1%, (iii) wash fraction 2: 200 mL, 0.047 g/L, 70.3%, (iv) wash fraction 3: 300 mL, 0.018 µL, 61.4%, and (v) wash fraction 4: 300 mL, 0.015 g/L, 63.3%. The wash fractions were not added to the product filtrate due to their low purity and concentration.

Figure 3:
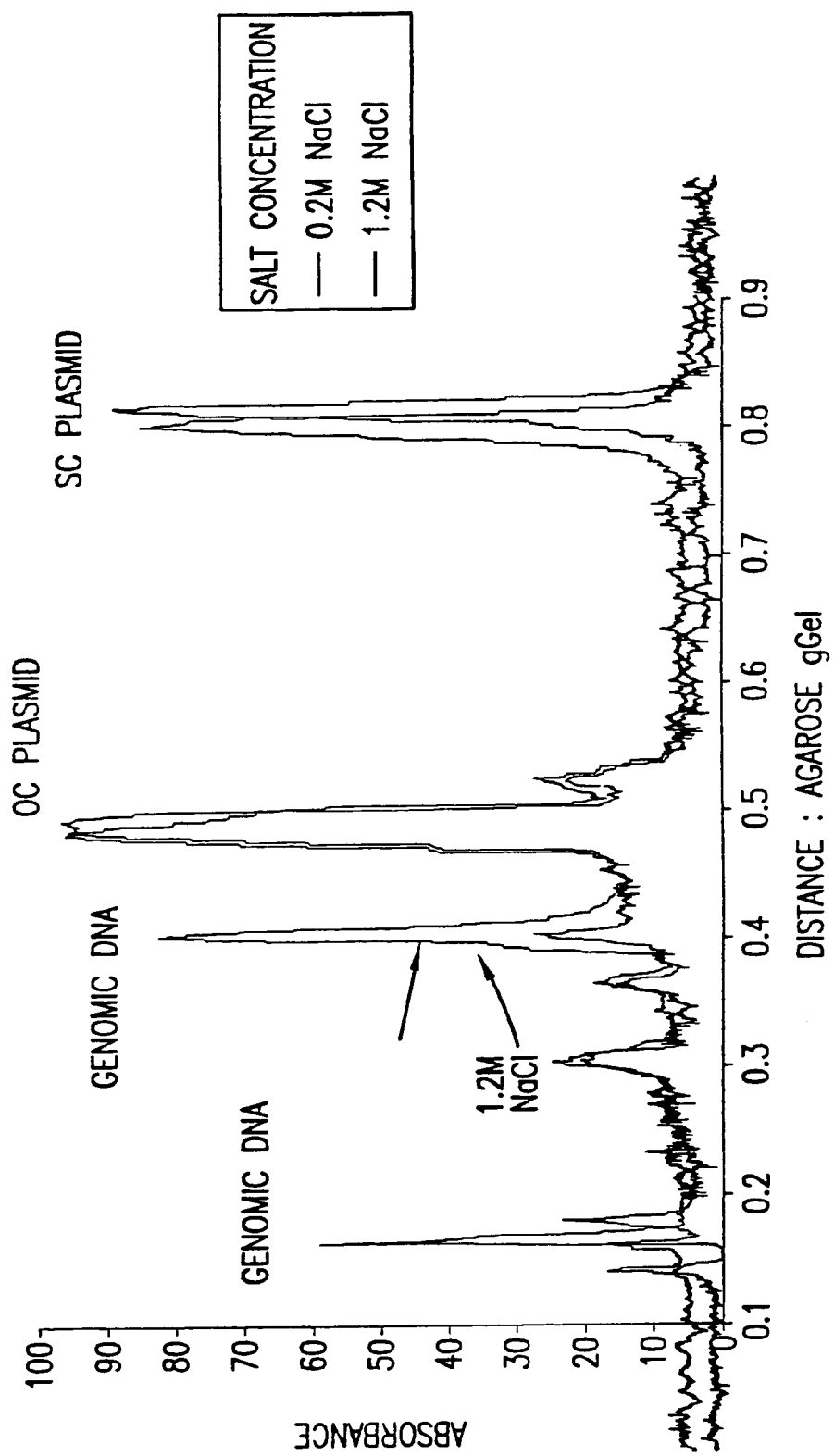
FIG. 3 shows selective dissolution of plasmid DNA by 0.2 M NaCl by agarose gel electrophoresis. Host, genomic DNA is only partially soluble and is removed by filtration after dissolving with 0.2 M NaCl. At 1.2 M NaCl, GDNA is soluble.

FIG. 3 shows selective dissolution of plasmid DNA by 0.2 M NaCl by agarose gel electrophoresis. Host, genomic DNA is only partially soluble and is removed by filtration after dissolving with 0.2 M NaCl. At 1.2 M NaCl, g DNA is soluble. A range from at least about 0.2M NaCl to at least about 2 M NaCl will be useful for selective dissolution of the CTAB precipitate.

Treating the batch with incremental amounts of LRA™—735 mL of redissolved precipitate in 0.5 M NaCl was added at room temperature to 45 g of LRA™ (Advanced Minerals). 500 mcL samples were taken at 4.8, 9.9, 19.1, and 19.6 hours. Table 1 depicts the total DNA concentrations and the composition of supercoiled plasmid DNA as measured by an analytical HPLC assay.

Periodically, incremental amounts of fresh LRA™ were added to the slurry and sample were taken at the following times:

(i) 4.6 g of LRA™ were added at 19.9 hr (for 35 g LRA™/g DNA). Samples were taken at 21.6, 23.8, and 25.4 hr;

(ii) 6.6 g of LRA™ were added at 25.8 hr (for 39.5 g LRA™/g DNA). Samples were taken at 26.8, 27.8, 28.8, and 30.9 hr;

(iii) 3.7 g of LRA™ were added at 32.2 hr (for 42 g LRA™/g DNA). Samples were taken at 32.4, 34.4, and 40.8 hr;

(iv) 3.98 g of LRA™ were added at 41 hr (for 45 g LRA™/g DNA). Samples were taken at 41.8, and 42.6 hr.

As depicted in Table 1, further increases in plasmid purity (as measured by an HPLC assay) can be correlated to the periodic additions of LRA™.

TABLE 1

Incremental addition of LRA ™

| Time (hr) | G LRA ™/gDNA | Total DNA Conc. (g/L) | Composition of Supercoiled Plasmid DNA (%) | Supercoiled Plasmid DNA Yield (%) |
|---|---|---|---|---|
| 0 | 0 | 1.93 | 93.0 | 100 |
| 4.8 | 31.7 | 1.93 | 93.5 | 100 |
| 9.9 | 31.7 | 1.81 | 92.6 | 93.4 |
| 19.1 | 31.7 | 1.89 | 96.3 | 102 |
| 19.6 | 31.7 | 1.89 | 91.9 | 96.5 |
| 21.6 | 35 | 1.97 | 93.7 | 103 |
| 23.8 | 35 | 1.96 | 95.6 | 104 |
| 25.4 | 35 | 1.96 | 94.0 | 102 |
| 26.8 | 39.5 | 1.80 | 93.9 | 94.1 |
| 27.8 | 39.5 | 1.83 | 95.5 | 97.6 |
| 28.8 | 39.5 | 1.68 | 95.2 | 89.4 |
| 30.9 | 39.5 | 1.91 | 95.8 | 102 |
| 32.4 | 42 | 1.86 | 96.2 | 99.5 |
| 34.4 | 42 | 1.82 | 96.3 | 97.6 |
| 40.8 | 42 | 1.83 | 96.3 | 98.2 |
| 41.8 | 45 | 1.68 | 97.9 | 91.9 |
| 42.6 | 45 | 1.64 | 97.1 | 88.7 |

FIG. 4A shows that optimum plasmid adsorption to calcium silicate occurs at a NaCl concentration of about 0.6M, when compared to higher NaCl concentrations. It will be within the purview of the skilled artisan to manipulate the NaCl concentration within this indicated range without effecting the ability of LRA™ to adsorb supercoiled plasmid DNA. Optimization of this step would involve an investigation of all factors which pertain to the underlying phenomenon of hydrogen bonding, hydrophobic and electrostatic interactions. Among such variables are salt concentration, type of salt, temperature, pH and type of adsorbent. For example, other calcium based adsorbents which bind DNA could be expected to afford separation under an optimization scheme involving the above solution phase variables.

Removing and washing the LRA™—After 42.9 hr, the LRA™ slurry was centrifuged at 19° C. and 8 kRPM for 25 min. The resulting 400 mL supernatant was collected. 200 mL of fresh 0.5 M NaCl was added to LRA™ pellet. A sterile spatula and vigorous shaking for 10 sec were used to resuspend the LRA™ pellet. The resuspended LRA™ was subjected to centrifugation for 10 min at 8 kRPM. The supernatants were collected, and LRA™ pellet was washed twice more in this fashion. The first supernatant (400 mL) and the three washes (3×200 mL) were assayed for total DNA concentration and composition of supercoiled plasmid DNA. Results are depicted in Table 2. Washes were not added to the product supernatant. The product supernatant was then sterile filtered through a 0.8-micron disposable vacuum filter unit to remove residual LRA™.

TABLE 2

Supernatant from centrifuged LRA ™ slurry and washes

| Sample | Volume (mL) | Total DNA Conc. (mg/mL) | Composition of Supercoiled Plasmid DNA (%) | Supercoiled Plasmid DNA Mass (g) |
|---|---|---|---|---|
| Reconst'd. CTAB Ppt. | 735 | 1.93 | 93.0 | 1.32 |
| Supernatant | 400 | 1.80 | 97.1 | 0.70 |
| Wash 1 | 200 | 0.89 | 92.6 | 0.16 |
| Wash 2 | 200 | 0.55 | 84.1 | 0.09 |
| Wash 3 | 200 | 0.36 | 72.5 | 0.05 |

Figure 4B:
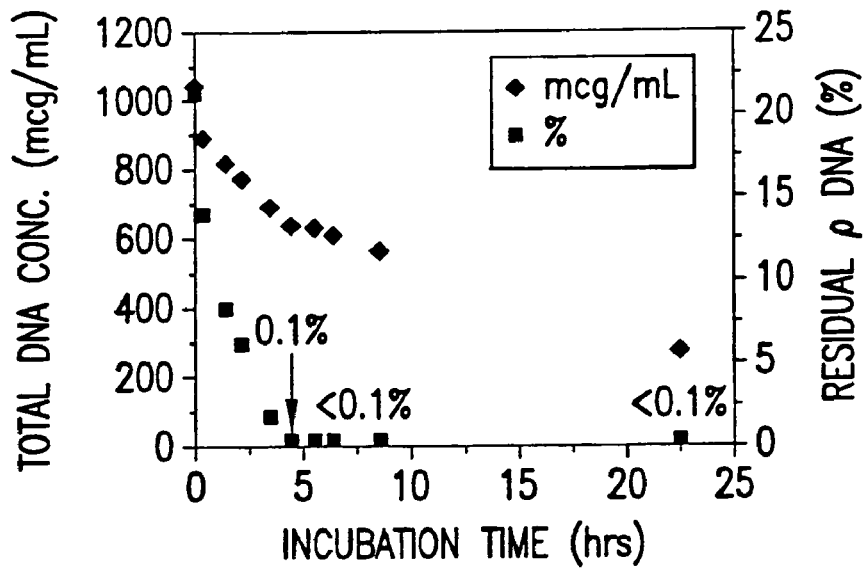
Figure 4C:
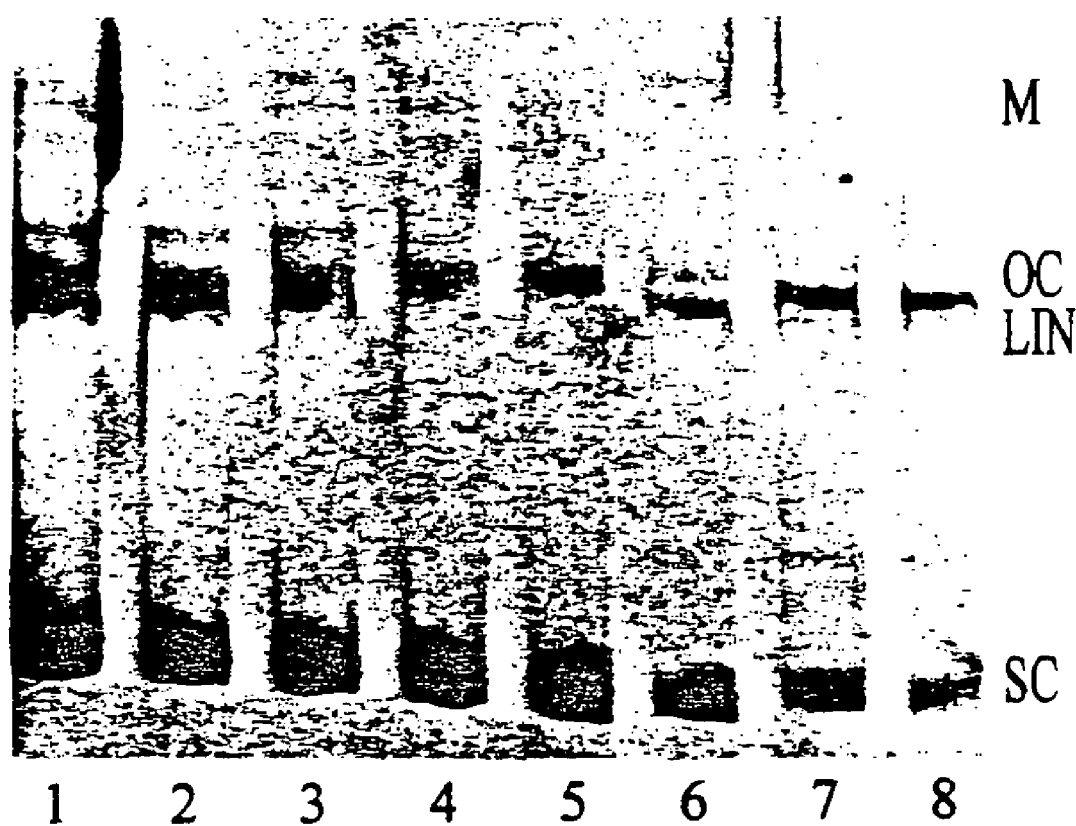
Figure 4D:
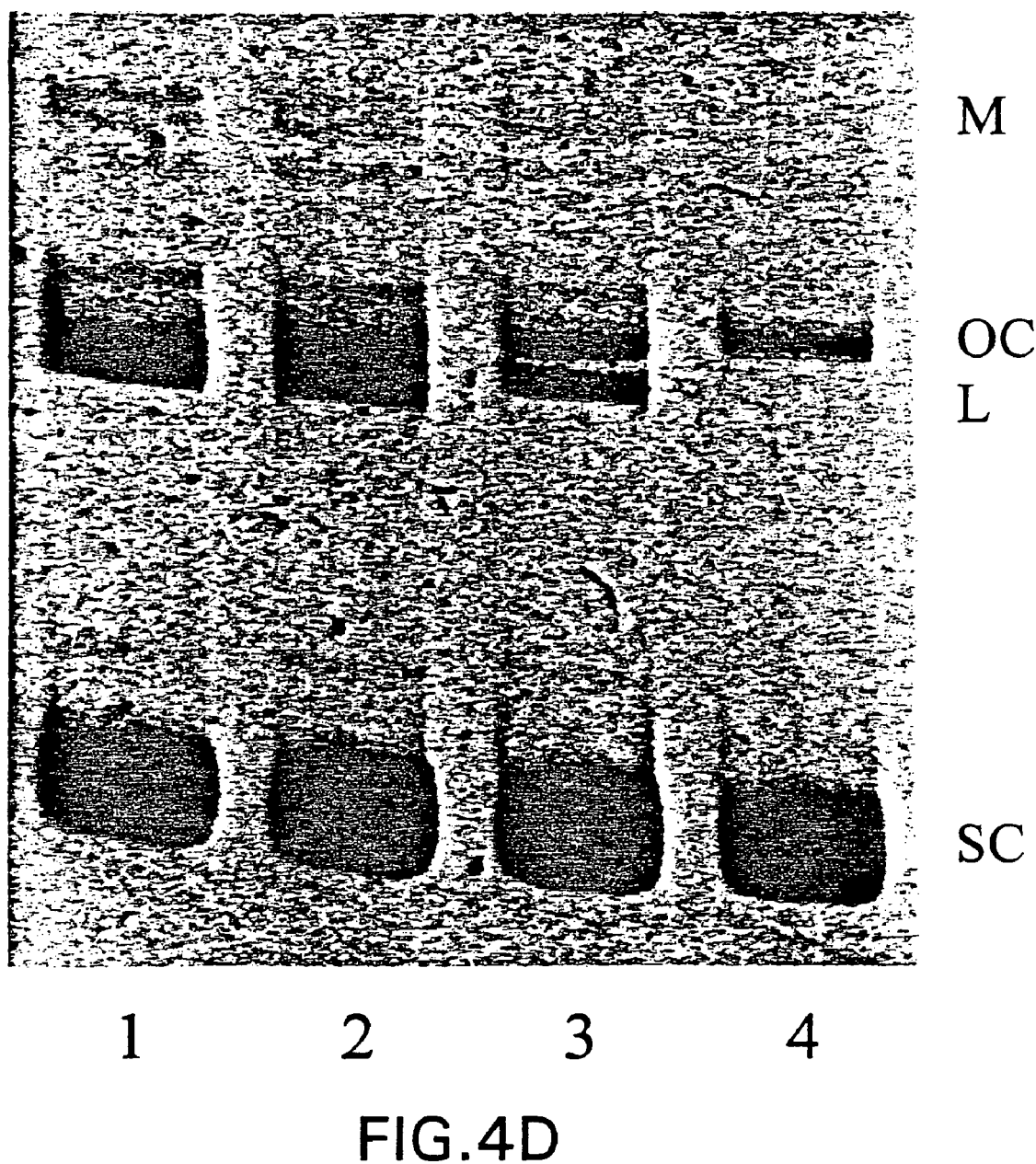

FIG. 4B shows the adsorption of genomic or host DNA over time. More specifically, this data shows that LRA™ selectively removes DNA after 5 hrs. of mixed contacting at 1.2 M NaCl concentration, resulting in a plasmid yield of about 60%. FIG. 4C is an agarose gel electrophoresis of liquid-phase samples during LRA™ contacting at 1.2 M NaCl. This data shows the removal of linear (Lin), relaxed open circle (OC) and multimers (M) are removed, while supercoiled plasmid DNA (SC) remains. Lanes 1-5 represent increasing time points and lanes 6-8 represent washes of filtered LRA™. FIG. 4D shows the selective adsorption of plasmid degradates onto hcCaSiO$_3$ in 0.5 M NaCl. Agarose gel electrophoresis of liquid-phase samples in contact with 32 g of hcCaSiO$_3$ per g of total DNA as a function of time are shown.

Ethanol precipitation of LRA™ product—400 mL of absolute ethanol was slowly added to 400 mL of post-LRA™ filtrate. The addition of ethanol was completed over a 2 hr period, yielding a final ethanol concentration of 50% v/v. The solution became very cloudy in the range of 36 to 38% v/v ethanol. At this point, ethanol addition was stopped for 30 min to allow for particle growth. Close inspection revealed fine, filterable particles. After a 30 minute mixed age, the suspension was filtered over a sterile 0.22-micron filter (Millipore, GP express membrane, 50 cm$^2$). Approximately 500 mL of absolute ethanol were used to wash the cake. The filter unit was then transferred to a vacuum oven and dried for 2 hr at 27° C. and 29 in Hg. 730 mg of dried powder was collected and stored in a sterile, tinted glass vial at −20° C.

Table 3 summarizes purity and yield (as measured by an analytical HPLC assay) at each step of the process. Yields of approximately 100% were achieved across low-cut CTAB, high-cut CTAB, and redissolution of high cut precipitate.

Table 4 summarizes the clearance of protein and endotoxin. Final ethanol-precipitated product is assayed for clearance of residual RNA, genomic DNA, endotoxin, protein, CTAB, lysozyme, LRA™, and Celpure P300.

TABLE 3

Purity and yield at each step of the process

| Sample | Volume (mL) | DNA conc. (mg/mL) | SC purity (%) | SC conc. (mg/mL) | SC mass (mg) | Step yield (%) | Cumulative yield (%) |
|---|---|---|---|---|---|---|---|
| UCL | 5600 | — | — | — | — | — | — |
| CL | 5050 | 0.338 | 83.6 | 0.283 | 1429 | 100.0 | 100.0 |

TABLE 3-continued

Purity and yield at each step of the process

| Sample | Volume (mL) | DNA conc. (mg/mL) | SC purity (%) | SC conc. (mg/mL) | SC mass (mg) | Step yield (%) | Cumulative yield (%) |
|---|---|---|---|---|---|---|---|
| LCF | 6440 | 0.265 | 83.6 | 0.222 | 1429 | 100.0 | 100.0 |
| HCF | 7100 | 0.0 | — | 0.0 | 0.0 | — | — |
| RHCP | 800 | 1.933 | 93.0 | 1.798 | 1438 | 100.6 | 100.6 |
| RHCP* | 735 | 1.933 | 93.0 | 1.798 | 1322 | 92.5 | 92.5 |
| Post LRA ™ | 400 | 1.800 | 97.1 | 1.748 | 699 | 52.8 | 48.9 |

UCL: unclarified lysate.
CL: diatomaceous earth clarified lysate.
LCF: CTAB low cut filtrate.
HCF: CTAB high cut filtrate, as expected contains no DNA.
RHCP: redissolved high cut precipitate in 0.5 M NaCl.
RHCP*: 735 mL feed to LRA ™ step, approximately 65 mL were used in LRA ™ probe studies.
Post LRA ™: 0.8 micron filtrate following LRA ™ adsorption step.
Analytical HPLC assay was used to measure DNA conc., SC purity, and SC conc.

TABLE 4

Clearance of protein, endotoxin, and RNA

| | Protein | | Endotoxin | | RNA | |
|---|---|---|---|---|---|---|
| Sample | (mg/mL) | (mg/mg SC) | (EU/mL) | (EU/mg SC) | (mg/mL) | (mg/mg SC) |
| CL | 0.937 | 3.311 | 1.2e5 | 4.2e5 | 1.00 | 3.55 |
| LCF | 0.709 | 3.193 | 9.2e6 | 4.1e7 | 0.714 | 3.22 |
| HCF | 0.625 | — | NA | — | 0.647 | — |
| RHCP | 0.049 | 0.027 | 1.1e5 | 6.1e4 | 0.093 | 0.052* |
| Post LRA ™ | LOD | — | 0.05 | 0.03 | 0.075 | 0.043* |

Sample descriptions are listed in Table 3. LOD: limit of detection. NA: not assayed. Protein content was measured using the Lowry method. Endotoxin content was measured using the LAL assay. *RNA concentration was measured using the Orcinol assay. High concentrations of plasmid DNA interfere with the Orcinol assay; this interference is reflected in RNA concentrations listed for RHCP and Post LRA ™ samples. The final product A260/A280 ratio was 1.9, an indication of low fractional RNA content.

Figure 6:
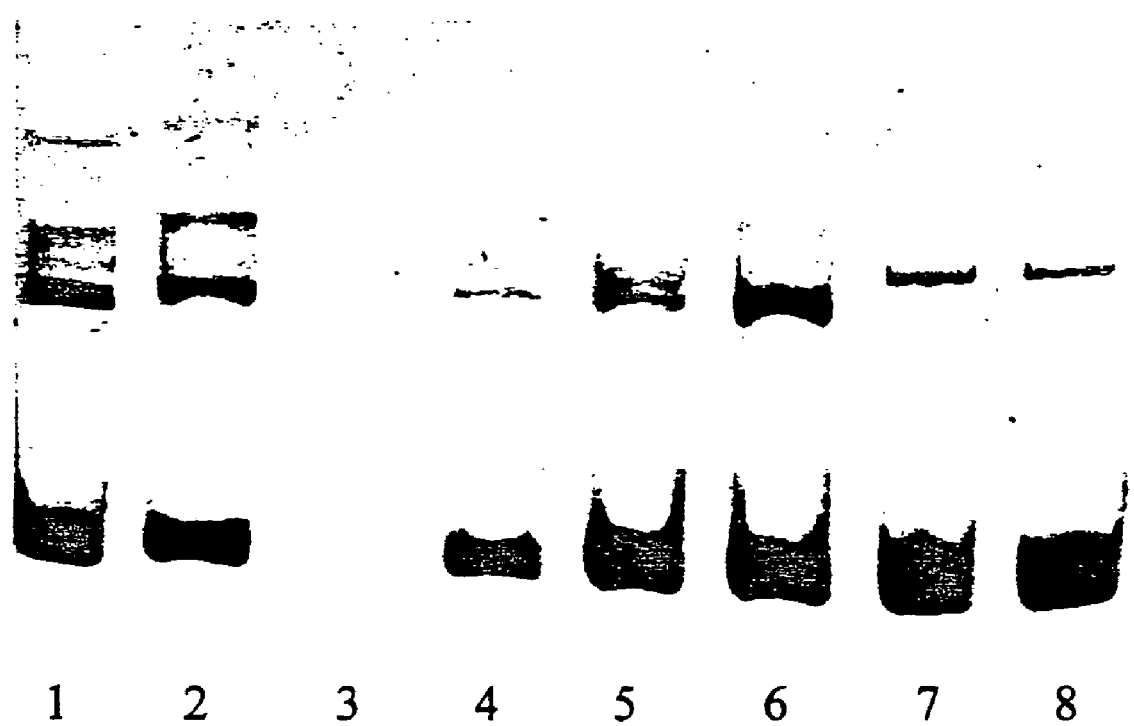
FIG. 6 shows the DNA composition of samples from process steps disclosed in Example section 1. Supercoiled plasmid is visualized in the lowest band. The higher bands represent various DNA impurities, including open circle and linear plasmid, plasmid multimers, and genomic DNA. Depicted is diatomaceous earth clarified lysate (lane 1, from left); low-cut filtrate at 0.23% w/v CTAB (lane 2); high-cut filtrate at 0.30% w/v CTAB, containing no DNA (lane 3); high-cut precipitate in 0.4 M NaCl (lane 4); high-cut precipitate in 0.475 M NaCl (lane 5); high-cut precipitate in 0.5 M NaCl (lane 6); 0.8-micron filtrate following hcCaSiO$_3$ adsorption step (lane 7); hcCaSiO$_3$ product subjected to ethanol precipitation and redissolution in sterile water (lane 8).

FIG. 6 illustrates the DNA composition of samples from process steps described in this Example section. Supercoiled plasmid is visualized in the lowest band. The higher bands represent various DNA impurities, including open circle and linear plasmid, plasmid multimers, and genomic DNA. Depicted is diatomaceous earth clarified lysate (lane 1, from left); low-cut filtrate at 0.23% w/v CTAB (lane 2); high-cut filtrate at 0.30% w/v CTAB, containing no DNA (lane 3); high-cut precipitate in 0.4 M NaCl (lane 4); high-cut precipitate in 0.475 M NaCl (lane 5); high-cut precipitate in 0.5 M NaCl (lane 6); 0.8-micron filtrate following LRA adsorption step (lane 7); LRA product subjected to ethanol precipitation and redissolution in sterile water (lane 8). A comparison of lanes 1 and 8 reveals that there is a substantial reduction in DNA degradate type impurities.

EXAMPLE 2

Use of a Particle-Size Analyzer to Monitor CTAB Precipitation

Figure 5:
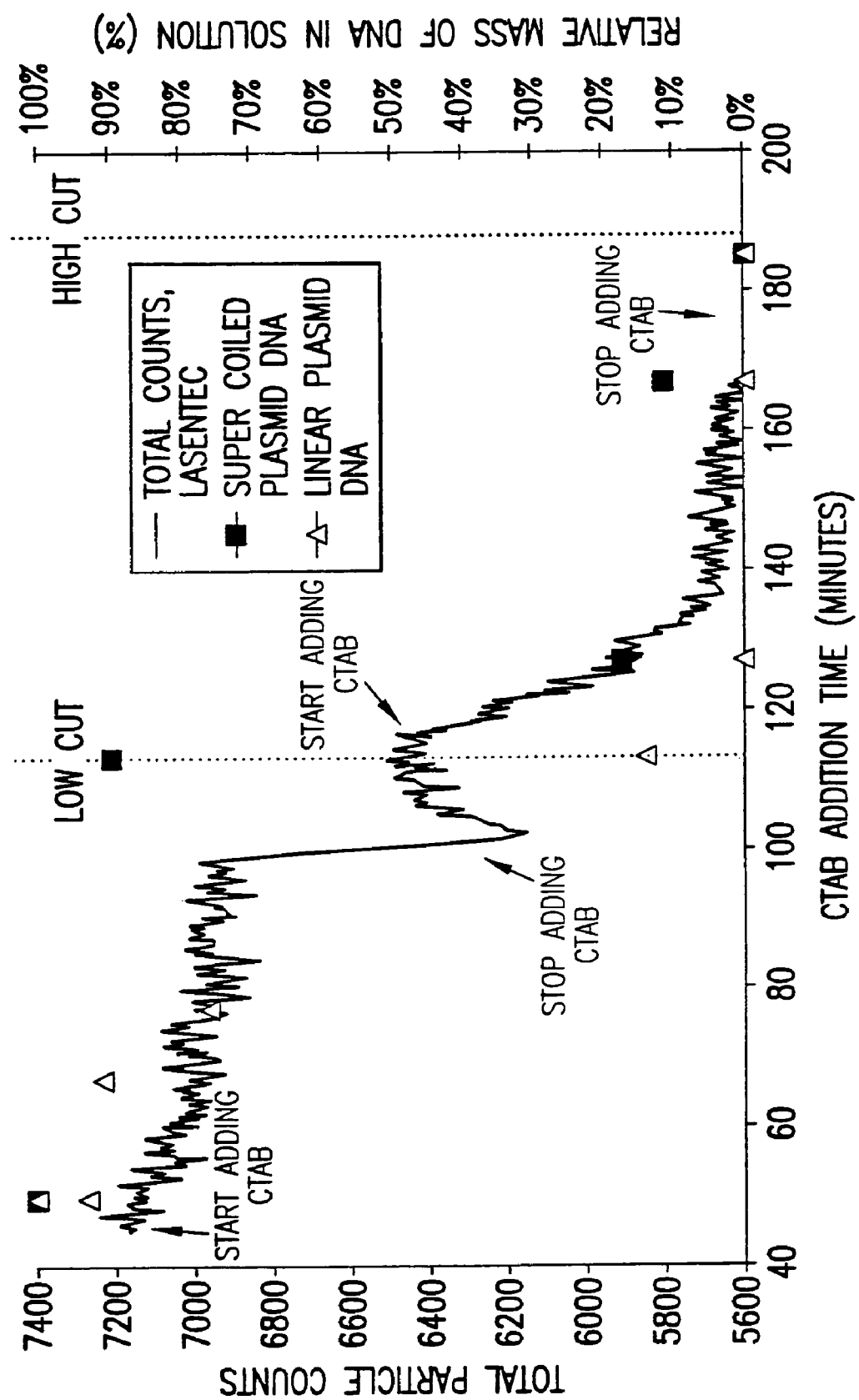
FIG. 5 shows precipitation of impurities by 0.25-0.30% w/v CTAB using Lasentec® particle size analyzer. The addition of 1% w/v CTAB in 40 mM NaCl to clarified lysate in STET buffer is stopped at 100 minutes based on abrupt change in particle counts. Precipitated impurities are removed by filtration. Additional CTAB is added to precipitate the supercoiled plasmid.

CTAB precipitation may be closely monitored using, for example a Lasentec® particle-size analyzer. Residual, finely divided cell debris and other impurities, including genomic DNA and relaxed circular and linear DNA degradates are precipitated from the clarified lysate by adding a solution of 1.0% w/v CTAB in 40 mM NaCl to a final concentration of 0.25-0.28% w/v CTAB. Precipitation of the impurities is monitored in real-time using a Lasentec® particle-size analyzer. Addition of CTAB is stopped after the total particle counts drop sharply. This is just enough CTAB to precipitate linear and relaxed circular DNA while leaving the supercoiled DNA in solution. The batch is then filtered to remove the precipitated impurities. CTAB is added to the batch to a final concentration of 0.30-33% w/v CTAB to precipitate the supercoiled DNA. FIG. 5 shows precipitation of impurities by 0.25-0.30% w/v CTAB using a Lasentec® particle size analyzer. CTAB addition is stopped at 100 minutes based on abrupt change in particle counts. Precipitated impurities are removed by filtration. Additional CTAB is added to precipitate the supercoiled plasmid.

EXAMPLE 3

Purification of Plasmid DNA From Approximately 80 L Fermentation Broth

Table 5 summaries a pilot lot utilizing the methodology disclosed in the present invention. The lot was started by resuspending roughly 15.9 L of harvested cells in STET buffer at a 1:10 dilution. Note that 15.9 L of harvested cells translated to roughly 80 L of fermentation broth. The STET-resuspended cells were incubated for 1 hour at 37° C. with Ready-Lyse lysozyme (Epicentre) at 500 U/mL. Cells were heat-lysed following the 37° C. incubation and were immediately cooled using two heat exchangers in series. The first was used heat the cells to 70° C., and the second was used to cool the cells to roughly 20° C. Celpure P300 was mixed into the lysate at a body feed concentration of approximately 40 g/L. The resulting slurry was filtered though a 25-micron stainless steel filter cloth. Filtrate was recirculated until a clarity of <25 NTU was achieved. The filter cake was dried using pressurized air to maximize filtrate recovery.

Celpure P300 was slurried into the clarified lysate at a body feed concentration of roughly 10 g/L. A low cut CTAB precipitation step was performed by adding 27.65 L of 2% (w/v) CTAB in 40 mM NaCl to the clarified lysate. CTAB was added in sub-surface mode over a period of two hours. Following the addition of CTAB, the low cut slurry was filtered though a 25-micron stainless steel filter cloth, and low cut filtrate was recirculated until a clarity of <10 NTU was achieved. The cake was again dried using pressurized air.

Celpure P300 was then slurried into the low cut filtrate at a body feed concentration of roughly 10 g/L. A high cut CTAB precipitation step was performed by adding 6.4 L of 2% (w/v) CTAB in 40 mM NaCl to the clarified lysate in sub-surface mode over a two hour period. This second high of CTAB caused the precipitation of plasmid DNA. The high cut slurry was then filtered through a 25-micron stainless steel filter cloth, and filtrate was recirculated until a clarity of <10 NTU was achieved. Pressurized air was used to dry the filter cake. The filter cake was then reslurried washed using 59.9 L of deionized water and filtered through a 25-micron stainless steel filter cloth. The initial filtrate was recirculated, and pressurized air was used to dry the filter cake.

Precipitated DNA in the wash filter cake was redissolved by adding 0.75 M NaCl and filtered through a 25-micron stainless steel filter to remove Celpure P300. As above, the initial filtrate was recirculated, and pressurized air was used to dry the filter cake. The salt concentration of the 0.75 M NaCl filtrate was adjusted to 3 M NaCl. Product was then stored at 4° C. and filtered at 4° C. through a 0.5-micron Milligard filter (Millipore). A 107 L from a total of 115 L of the 4° C. filtrate were warmed to 20° C., and 2.43 kg of LRA (Advanced Minerals) were added. After roughly 23 hours, the LRA was removed via filtration with a 0.45-micron Durapore (Millipore) filter media.

0.5 M EDTA was spiked into the LRA filtrate to a final concentration of 20 mM EDTA. The LRA filtrate was then concentrated using ultrafiltration (100k regenerated cellulose, Millipore) to 3 g/L. The concentrated LRA filtrate diafiltered versus 3 diafiltration volumes of 20 mM NaCl with 20 mM EDTA and 7 diafiltration volumes of 20 mM NaCl. 5 M NaCl was spiked into the product to increase the salt concentration to 150 mM NaCl. Product was then diafiltered versus 3 diafiltration volumes of 150 mM NaCl. Product was then further concentrated to a volume of roughly 3 L and drained from the ultrafiltration system. The membrane was washed twice with 250 mL aliquots of 150 mM NaCl. The product and membrane washes were pooled yielding roughly 3.5 L of final product at 7.6 g/L. Final product was 0.22-micron sterile filtered. As indicated in parentheses in Table 5 below, 107 L of 115 L of redissolved product (following a 4° C. filtration) were used in the LRA step.

TABLE 5

Purity and Yield at Each Step of the Process of Example 3

| | Volume (L) | Plasmid DNA Conc. (g/L) | Plasmid DNA mass (g) | Step Yield (%) | Net Yield (%) |
|---|---|---|---|---|---|
| Clarified lysate | 133 | 0.41 | 55 | 84 | 84 |
| Low cut filtrate | 157 | 0.30 | 47 | 85 | 71 |
| High cut filtrate | 160 | 0 | 0 | — | — |
| Redissolved product | 115 (107) | 0.42 (0.42) | 48 (45) | 102 | 73 |
| LRA filtrate | 96.6 | 0.30 | 29 | 64 | 47 |
| UF product | 3.5 | 7.6 | 27 | 93 | 44 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A method of purifying supercoiled plasmid DNA from a cell lysate of a large scale microbial fermentation which comprises adding hydrated, crystallized calcium silicate to the cell lysate to adsorb residual impurities away from the supercoiled plasmid DNA.

2. A method of claim 1 wherein the cell lysate is clarified prior to addition of the hydrated, crystallized calcium silicate.

3. A method of claim 2 wherein the cell lysate is clarified by addition of diatomaceous earth.

4. A method of claim 3 wherein the supercoiled plasmid DNA is further concentrated by a process selected from the group consisting of alcohol precipitation and ultrafiltration.

5. A method of claim 4 wherein the supercoiled plasmid DNA is concentrated by ethanol precipitation.

6. A method of claim 1 wherein the supercoiled plasmid DNA is further concentrated by a process selected from the group consisting of alcohol precipitation and ultrafiltration.

7. A method of claim 6 wherein the supercoiled plasmid DNA is concentrated by ethanol precipitation.

8. A method of claim 1 wherein the hydrated, crystallized calcium silicate is added in a stepwise manner.

9. A method of claim 8 wherein the cell lysate is clarified by addition of diatomaceous earth.

10. A method of claim 9 wherein the supercoiled plasmid DNA is further concentrated by a process selected from the group consisting of alcohol precipitation and ultrafiltration.

11. A method of claim 10 wherein the supercoiled plasmid DNA is concentrated by ethanol precipitation.

12. A method of claim 1 wherein the hydrated, crystallized calcium silicate has a surface area of greater than about 75 $m^2/g$.

13. A method of claim 12 wherein the hydrated, crystallized calcium silicate is in a composition comprising 25-35% calcium oxide by weight and 45-55% silicon dioxide by weight.

* * * * *